(12) United States Patent
Bashirians et al.

(10) Patent No.: US 8,835,183 B2
(45) Date of Patent: Sep. 16, 2014

(54) DETERMINATION OF SFLT-1:ANGIOGENIC FACTOR COMPLEX

(75) Inventors: George Bashirians, Penfield, NY (US); Deborah Byrne, Rochester, NY (US); Sarah Groulx, Ontario, NY (US); Sharon Jackson, Rochester, NY (US); Heather Lane-Brown, Honeoye Falls, NY (US); Banumathi Sankaran, Pittsford, NY (US); Edward Scalice, Penfield, NY (US); Karen Yang, Edison, NJ (US); Jian Zheng, Raritan, NJ (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 587 days.

(21) Appl. No.: 12/350,090

(22) Filed: Jan. 7, 2009

(65) Prior Publication Data

US 2009/0176247 A1 Jul. 9, 2009

Related U.S. Application Data

(60) Provisional application No. 61/019,351, filed on Jan. 7, 2008.

(51) Int. Cl.
*G01N 33/543* (2006.01)
*G01N 33/68* (2006.01)
*G01N 33/566* (2006.01)

(52) U.S. Cl.
CPC .......... *G01N 33/6872* (2013.01); *G01N 33/543* (2013.01); *G01N 33/566* (2013.01); *G01N 2333/475* (2013.01); *G01N 2333/71* (2013.01); *G01N 2800/368* (2013.01); *G01N 2800/56* (2013.01)
USPC ............ 436/518; 435/7.92; 436/86; 436/501; 436/546

(58) Field of Classification Search
None
See application file for complete search history.

(56) References Cited

U.S. PATENT DOCUMENTS

| | | | |
|---|---|---|---|
| 7,314,734 B2 | 1/2008 | Maglione et al. | |
| 7,323,346 B2 | 1/2008 | Thadhani et al. | |
| 7,335,362 B2 | 2/2008 | Karumanchi et al. | |
| 7,344,892 B2 | 3/2008 | Thadhani et al. | |
| 7,407,659 B2 | 8/2008 | Karumanchi et al. | |
| 7,435,419 B2 | 10/2008 | Karumanchi et al. | |
| 2007/0010442 A1 | 1/2007 | Kendall et al. | |
| 2007/0111326 A1 | 5/2007 | Sogin et al. | |
| 2009/0155827 A1* | 6/2009 | Zeiher et al. | 435/15 |

FOREIGN PATENT DOCUMENTS

| | | | |
|---|---|---|---|
| WO | WO01/85796 | 11/2001 | |
| WO | WO2005/077007 | 8/2005 | |
| WO | WO2006/001888 | 1/2006 | |
| WO | WO 2006/045593 | * 5/2006 | ............ G01N 33/74 |
| WO | WO2006/069373 | 6/2006 | |
| WO | WO2006/128553 | 12/2006 | |
| WO | WO2008/005814 | 1/2008 | |

OTHER PUBLICATIONS

Yoshimatsu et al., Relationship between urinary albumin and serum soluble fms-like tyrosine kinase 1 (sFlt-1) in normal pregnancy, European Journal of Obstetrics & Gynecology and Reproductive Biology 128 (2006) pp. 204-208.*
Ahmad, Shakil, et al. "Placental Soluble VEGFR-1 Is Increased in Preeclampsia and Is Regulated by Hypoxia" J Soc Gynecol Investig, Jan./Feb. 2002, vol. 9, No. 1 (Supplement), p. 80A, Abstract #44.
Ahmad, Shakil, et al. "Elevated Placental Soluble Vascular Endothelial Growth Factor Receptor-1 Inhibits Angiogenesis in Preeclampsia" *Circulation Research*, Oct. 2004, vol. 95(9), pp. 884-891.
Chaiworapongsa, Tinnakorn, et al. "Evidence Supporting a Role for Blockade of the Vascular Endothelial Growth Factor System in the Pathophysiology of Preeclampsia" *American Journal of Obstetrics and Gynecology*, 2004, vol. 190, pp. 1541-1547.
Chaiworapongsa, Tinnakorn, et al. "Plasma Soluble Vascular Endothelial Growth Factor Receptor-1 Concentration Is Elevated Prior to the Clinical Diagnosis of Pre-eclampsia", *Journal of Maternal-Fetal and Neonatal Medicine*, Jan. 2005, vol. 17(1), pp. 3-18.
Chappell, Lucy, et al. "Prediction of Pre-Eclampsia in High Risk Women by a Combination of Biochemical Markers" J Soc Gynecol Investig, Jan./Feb. 2001, vol. 8, No. 1 (Supplement), p. 53A, Abstract #23.
Chmait, Ramen, et al. "The Differential Expression of VEGF and Its Receptor in the Dedicue of Preeclamptic Patients" J Soc Gynecol Investig, Jan./Feb. 2001, vol. 8, No. 1 (Supplement), p. 151A, Abstract #352.
Chmait, Ramen, et al. "Aberrant Placentation in Preeclampsia May Be Due in Part to the Action of Modulators of VEGF At the Maternal-Fetal Interface" J Soc Gynecol Investig, Jan./Feb. 2002, vol. 9, No. 1 (Supplement), p. 80A, Abstract #45.
Eriksson, A, et al. "Placenta growth-factor-1 antagonizes VEGF-induced angiogenesis and tumor growth by the formation of functionally inactive PlGF-1/VEGF heterodimers" *Cancer Cell*, (Feb. 2002), vol. 1, pp. 99-108.
Errico, Michela, et al. "Identification of placenta growth factor determinants for binding and activation of Flt-1 receptor" *J Biol Chem* (Oct. 2004), vol. 279, No. 42, pp. 43929-43929.

(Continued)

*Primary Examiner* — Gary W Counts
(74) *Attorney, Agent, or Firm* — Susan J. Timian (57) ABSTRACT

Methods for determining the presence or amount of a complex comprising a first and second molecular entity are provided, preferably an sFlt-1:PlGF complex. A determination of the presence or amount of the complex can be used in methods for predicting, detecting, monitoring a disease, or guiding therapy in respect to a disease such as vascular, vascular-related disease, cardiac, cardiac-related disease, cancer, cancer-related disease, preeclampsia, and preeclampsia-related disease. Determining sFlt-1:angiogenic factor complex is particularly useful for predicting and detecting preeclampsia in early stages of gestation and in stages of the disease where clinical evaluation may be uninformative.

5 Claims, 2 Drawing Sheets

(56) References Cited

OTHER PUBLICATIONS

Fry, Gordon, et al. "Concentrations of Growth Factors in Second-Trimester Maternal Serum As a New Method for Predicting Severe, Early-Onset Preeclampsia" J Soc Gynecol Investig, Jan./Feb. 2002, vol. 9, No. 1 (Supplement), p. 176A, Abstract #348.

Hertig, Alexandre, et al., "Maternal Serum sFlt1 Concentration Is an Early and Reliable Predictive Marker of Preeclampsia", *Clinical Chemistry*, 2004, vol. 50, No. 9, pp. 1702-1703.

Hornig C et al. "Detection and quantification of complexed and free soluble human vascular endothelial growth factor receptor-1 (sVEGFR-1) by ELISA" *J Immuno Methods* (Jun. 1999), vol. 226, Nos. 1-2, pp. 169-177.

Kim, Shin-Young, et al., "Increased sFlt-1 to PlGF Ratio in Women Who Subsequently Develop Preeclampsia", *J Korean Med Sci*, v 22, pp. 873-877 (2007).

Koga, Kaori, et al., ".Elevated Serum Soluble Vascular Endothelial Growth Factor Receptor 1 (sVEGFR-1) Levels in Women With Preeclampsia" *The Journal of Clinical Endocrinology & Metabolism*, 2003, 88(5), pp. 2348-2351.

Krysiak, Oliver, et al., "Soluble Vascular Endothelial Growth Factor Receptor-1 (sFLT-1) Mediates Downregulation of FLT-1 and Prevents Activated Neutrophils From Women With Preeclampsia From Additional Migration by VEGF", *Circ Res* v97 pp. 1253-1261 (2005).

Lam, Chun, et al., "Circulating Angiogenic Factors in the Pathogenesis and Prediction of Preeclampsia", *Hypertension* v 46 pp. 1077-1085 (2005).

Levine, Richard J., et al., "Urinary Placental Growth Factor and Risk of Preeclampsia", *JAMA* v 293 pp. 77-85 (2005).

Levine, Richard J., et al., "Circulating Angiogenic Factors and the Risk of Preeclampsia" *New England Journal of Medicine*, Feb. 12, 2004, 350;7 pp. 672-683.

Liu, Yu-Wang, et al., "Quantification of Soluble Vascular Endothelial Growth Factor Receptor-1 in Patients With Preeclampsia", Poster, The 15th World Congress, International Society for the Study of Hypertension in Pregnancy, Lisbon, Portugal Jul. 2006.

Luttun, Aernout and Carmeliet, Peter, "Soluble VEGF receptor Flt1: the elusive preeclampsia factor discovered?", *J Clin Invest* v 111, pp. 600-602 (2003).

Maynard, Sharon, et al., "Preeclampsia and Angiogenic Imbalance", *Annu Rev Med* v 59 pp. 61-78 (2008).

Maynard, Sharon E., et al., "Excess Placental Soluble fms-Like Tyrosine Kinase 1 (sFlt1) May Contribute to Endothelial Dysfunction, Hypertension, and Proteinuria in Preeclampsia", *The Journal of Clinical Investigation*, Mar. 2003, vol. 111, No. 5, pp. 649-658.

McKeeman, Gareth C., et al., "Soluble Vascular Endothelial Growth Factor Receptor-1 (sFlt-1) Is Increased Throughout Gestation in Patients Who Have Preeclampsia Develop", *American Journal of Obstetrics and Gynecology*, Mar. 1, 2004, 191, pp. 1240-1246.

Mutter, Walter P., et al., "Molecular mechanisms of preeclampsia", *Microvascular Research* v 75 pp. 1-8 (2008).

Rana, Sarosh, et al., "Angiogenic proteins as markers for predicting preeclampsia", *Expert Rev Obstet Gynecol* v 21 n 1 pp. 61-65 (2007).

Romero, Roberto, et al., "Changes in the Maternal Plasma Concentration of Two Angiogenic Factors—Placental Growth Factor and Angiogenin—Precede the Development of Pre-Eclampsia" J Soc Gynecol Investig, Jan./Feb. 2001, vol. 8, No. 1 (Supplement), p. 74A, Abstract #92.

Salahuddin, Saira, et al., "Diagnostic utility of soluble fms-like tyrosine kinase 1 and soluble endoglin in hypertensive diseases of pregnancy", *Am J Obstet Gynecol* (2007) v 197, 28.e1-28.e6.

Schmidt, Markus, et al., "Altered angiogenesis in preeclampsia: evaluation of a new test system for measuring placental growth factor", *Clin Chem Lab Med* v 45 n 11 pp. 1504-1510 (2007).

Shibata, Eiji, et al., "Soluble fms-Like Tyrosine Kinase 1 Is Increased in Preeclampsia But Not in Normotensive Pregnancies With Small-For-Gestational-Age Neonates: Relationship to Circulating Placental Growth Factor", *The Journal of Clinical Endocrinology & Metabolism*, 2005, vol. 90, pp. 4895-4903.

Widmer, Mariana, et al., "Mapping the Theories of Preeclampsia and the Role of Angiogenic Factors: A Systematic Review", *Obstetrics & Gynecology*, Jan. 2007, vol. 109(1), pp. 168-180.

Hornig, C., et al., "Release and Complex Formation of Soluble VEGRF-1 from Endothelial Cells and Biological Fluids", Laboratory Investigation 80(4):443-454 (2000).

\* cited by examiner

Figure 1

Figure 2 sFlt-1:PlGF Complex Assay
Dose Response Curve

DETERMINATION OF SFLT-1:ANGIOGENIC FACTOR COMPLEX

CROSS-REFERENCE TO RELATED APPLICATIONS

This application claims the benefit of U.S. Provisional Application No. 61/019,351, filed Jan. 7, 2008.

STATEMENT REGARDING FEDERALLY SPONSORED RESEARCH OR DEVELOPMENT

Not applicable.

FIELD OF THE INVENTION

The invention relates to immunoassays and in vitro diagnostics and particularly to sFlt-1:angiogenic factor complex determination including in preeclampsia.

BACKGROUND OF THE INVENTION

Preeclampsia is a syndrome of hypertension, edema, and proteinuria that affects 5 to 10% of pregnancies and results in substantial maternal and fetal morbidity and mortality. Preeclampsia accounts for 200,000 maternal deaths worldwide per year. Clinical symptoms of preeclampsia typically appear after the 20th week of pregnancy and are usually detected during routine evaluation of a woman's blood pressure and testing for the presence of protein in a sample of her urine. However, such clinical evaluation is ineffective for early diagnosis of the syndrome. Being able to evaluate the likelihood of developing preeclampasia, and/or being able to diagnose preeclampsia in an early stage of gestation, and/or being able to diagnose preeclampsia during a phase of the disease when clinical evaluation is uninformative, would allow early intervention and reduce the risk of medical complications and mortality for a pregnant woman and developing fetus.

Currently there are no known cures for preeclampsia. Preeclampsia can vary in severity from mild to life threatening. Maternal complications include renal failure, HELLP syndrome (hemolysis, elevated liver enzymes, and thrombocytopenia), liver failure, cerebral edema with seizures and rarely death. Potential fetal complications include low birth weight, prematurity and death. A mild form of preeclampsia can be treated with bed rest and frequent monitoring. For moderate to severe cases, hospitalization is recommended and blood pressure medication or anticonvulsant medications to prevent seizures are prescribed. If the condition becomes life threatening to the mother or the baby, the pregnancy is terminated and the baby is delivered pre-term.

Molecular mechanisms associated with preeclampsia have recently been reviewed (Mutter and Karumanchi, Microvascular Research 75:1-8, 2008). As stated by Mutter and Karumanchi, it is believed that endothelial dysfunction contributes to the clinical syndrome of preeclampsia (Roberts and Cooper, Lancet 357:53-56, 2001). Many of the symptoms of the disease may result from aberrant endothelial function (including arterial hyperreactivity to exogenous and endogenous stimuli, proteinuria related to increased glomerular permeability, cerebral edema and increased CNS permeability, as well as vascular thrombosis resulting in the HELLP syndrome) (Roberts, Semin Reprod Endocrinol 16:5-15, 1998; Roberts and Cooper, Lancet 357:53-56, 2001). As such, there has been an active search for circulating factors that cause or contribute to endothelial dysfunction.

Proper development of the fetus and placenta is mediated by several growth factors. One of these growth factors is vascular endothelial growth factor (VEGF). VEGF is an endothelial cell-specific mitogen, an angiogenic inducer, and a mediator of vascular permeability. VEGF has also been shown to be important for glomerular capillary repair. VEGF binds as a homodimer to one of two homologous membrane-spanning tyrosine kinase receptors—the fms-like tyrosine kinase receptor (Flt-1) (also known as vascular endothelial growth factor receptor 1 or VEGF-R1), and the kinase domain region receptor (Flk/KDR) (also known as vascular endothelial growth factor receptor 2 or VEGF-R2) which are differentially expressed in endothelial cells obtained from many different tissues. Flt-1, but not Flk/KDR, is highly expressed by trophoblast cells which contribute to placenta formation. Placenta growth factor (PlGF) is a VEGF family member that is also involved in placenta development. PlGF is expressed by cyto- and syncytiotrophoblasts and is capable of inducing proliferation, migration, and activation of endothelial cells. PlGF binds to as a homodimer to the Flt-1 receptor, but not the Flk/KDR receptor. Both PlGF and VEGF contribute to the mitogenic activity and angiogenesis that are critical for the developing placenta.

A soluble form of the Flt-1 receptor (sFlt-1) has been identified in a cultured medium of human umbilical vein endothelial cells and in vivo expression was subsequently demonstrated in placenta tissue. sFlt-1 is a splice variant of the Flt-1 receptor which lacks the transmembrane and cytoplasmic domains (He et al., Mol Endocrinol 13:537-545, 1999; Kendall and Thomas, Proc Natl Acad Sci USA 90:10705-10709, 1993).

Recent work by researchers at Beth Israel Deaconess Medical Center and Harvard Medical School has demonstrated increased placental production and maternal serum levels of sFlt-1 in patients with preeclampsia (Ahmad and Ahmed, Circ Res 95:884-891, 2004; Chaiworapongsa et al., Am J Obstet Gynecol 190:1541-1547, 2004; Koga et al., J Clin Endocrinol Metab 88:2348-2351, 2003; Maynard et al., J Clin Invest 111:649-658, 2003; Shibata et al., J Clin Endocrinol Metab 90:4895-4903, 2005). sFlt-1 is able to bind both VEGF and PlGF. Free in serum, it may diminish binding of these growth factors to their cognate receptors Flt-1 and Flk/KDR respectively (Kendall et al., Biochem Biophys Res Commun 226:324-328, 1996). In addition to VEGF and PlGF, the placenta is known to produce a number of other angiogenic factors, including the angiopoietins (Ang-1 and Ang-2) as well as their receptor Tie-2 (Dunk et al., Am J Pathol 156:2185-2199, 2000; Geva et al., J Clin Endocrinol Metab 87:4213-4224, 2002; Goldman-Wohl et al., Mol Hum Reprod 6:81-87, 2000). Increased levels of sFlt-1 and decreased levels of VEGF and PlGF are found in serum of women with preeclampsia.

Recent attention has also focused on another factor, endoglin (Eng), a co-receptor for transforming growth factor $\beta1$ and $\beta3$, and a protein expressed in large quantities by the placenta in preeclampsia. The extracellular domain of endoglin may be shed and is found in the serum where it is referred to as soluble endoglin (sEng). Like sFlt-1, sEng is increased in maternal serum 2 to 3 months prior to the onset of disease (Levine et al., N Engl J Med 355:992-1005, 2006).

The identification of an imbalance of circulating angiogenic factors that precedes the onset of preeclampsia or its clinical manifestation will be useful in designing screening and/or diagnostic tests to identify patients at risk for preeclampsia. Such a test would be invaluable to clinicians who may offer close follow-up and therapeutic interventions early in the course of disease. Several retrospective studies using serum obtained from patients having been afflicted with preeclampsia have shown that sFlt-1 concentrations in serum are high as much as 5 to 6 weeks before any clinical findings are noted (Chaiworapongsa et al., J Matern Fetal Neomatal Med 17:3-18, 2005; Hertig et al., Clin Chem 50:1702-1703, 2004; Levine et al., N Engl J Med 350:672-683, 2004; McKeeman et al., Am J Obstet Gynecol 191:1240-1246, 2004). In addition, free VEGF and PlGF are low (Hertig et al., Clin Chem 50:1702-1703, 2004; Levine et al., N Engl J Med 350:672-683, 2004). A recent systematic review of the literature to assess if elevated sFlt-1 or decreased PlGF in the serum could accurately predict the onset of preeclampsia concluded that third trimester increases in sFlt-1 and decrease in PlGF are associated with preeclampsia but there is currently insufficient data to recommend these as screening tests (Widmer et al., Obstet Gynecol 109:168-180, 2007).

A need continues to exist for more efficient and/or more effective methods of predicting a woman's risk for developing preeclampsia or determining if a woman has preeclampsia. Predicting and/or detecting preeclampsia in an early stage of gestation and/or in a stage of the disease where clinical evaluation may be uninformative would be particularly advantageous.

BRIEF SUMMARY OF THE INVENTION

In one aspect, the invention relates to a method of determining the presence or amount of sFlt-1:PlGF complex. The method comprises:

a) capturing the complex with capture agent that binds to PlGF, and detecting the complex with detector agent that binds to one or both of sFlt-1 and sFlt-1:PlGF complex; or b) capturing the complex with capture agent that binds to sFlt-1, and detecting the complex with detector agent that binds to one or both of PlGF and sFlt-1:PlGF complex; or c) capturing the complex with capture agent that binds to sFlt-1:PlGF complex, and detecting the complex with detector agent that binds to sFlt-1:PlGF complex, wherein capture agent and detector agent are capable of being bound simultaneously to the complex; or d) capturing the complex with capture agent that binds to sFlt-1:PlGF complex, and detecting the complex with detector agent that binds to one or both of PlGF and sFlt-1.

In another aspect, the invention relates to a method of guiding therapy of, or predicting, detecting, or monitoring, vascular, vascular-related, cancer, cancer-related, cardiac, cardiac-related, preeclampsia or preeclampsia-related disease in an individual. The method comprises:

a) determining the presence or amount of sFlt-1:PlGF complex in a sample from an individual; and b) i) comparing the result of the sFlt-1:PlGF determination with one or more reference values; or ii) converting the result of the sFlt-1:PlGF complex determination into one or more transformed results, using one or more mathematical operations or one or more algorithms, and comparing the sFlt-1:PlGF complex transformed results with one or more reference values;

thereby guiding therapy of, or predicting, detecting, or monitoring, the disease.

In one embodiment, the method may further comprise:

a) determining the presence or amount of one or more molecular entities in the sample; and b) i) comparing the result of the molecular entities determination and the result of the sFlt-1:PlGF complex determination with the one or more reference values; or ii) converting the result of the molecular entities determination and the result of the sFlt-1:PlGF complex determination into one or more transformed results, using one or more mathematical operations or one or more algorithms, and comparing the molecular entities transformed results and the sFlt-1:PlGF transformed results with the one or more reference values.

In yet another embodiment, the method may further comprise:

a) determining the values of one or more physical attributes of the individual; and b) i) comparing the physical attributes determination and the result of the molecular entities determination and the result of the sFlt-1:PlGF complex determination with the one or more reference values; or ii) converting the physical attributes determination and the result of the molecular entities determination and the result of the sFlt-1:PlGF complex determination into one or more transformed results, using one or more mathematical operations or one or more algorithms, and comparing the physical attributes transformed results and the molecular entities transformed results and the sFlt-1:PlGF transformed results with the one or more reference values.

In an additional embodiment, the method may comprise:

a) determining the values of one or more physical attributes of the individual; and b) i) comparing the physical attributes determination and the result of the sFlt-1:PlGF complex determination with the one or more reference values; or ii) converting the physical attributes determination and the result of the sFlt-1:PlGF complex determination into one or more transformed results, using one or more mathematical operations or one or more algorithms, and comparing the physical attributes transformed results and the sFlt-1:PlGF transformed results with the one or more reference values.

Another aspect of the invention relates to a composition for determining the presence or amount of sFlt-1:PlGF complex. The composition comprises:

a) capture agent that binds to PlGF and detector agent that binds to one or both of sFlt-1 and sFlt-1:PlGF complex; or b) capture agent that binds to sFlt-1 and detector agent that binds to one or both of PlGF and sFlt-1:PlGF complex; or c) capture agent that binds to sFlt-1:PlGF complex and detector agent that binds to sFlt-1:PlGF complex, wherein capture agent and detector agent are capable of being bound simultaneously to the complex; or d) capture agent that binds to sFlt-1:PlGF complex and detector agent that binds to one or both of PlGF and sFlt-1.

Additionally, the invention relates to a composition comprising a purified form of sFlt-1:PlGF complex.

DETAILED DESCRIPTION OF THE INVENTION sFlt-1, as used herein, refers to the soluble form of the fms-like tyrosine kinase receptor (Flt-1). Flt-1 is also known as vascular endothelial growth factor receptor 1 (VEGFR-1). sFlt-1 (also known as sVEGFR-1) is a splice variant of Flt-1 which lacks the transmembrane and cytoplasmic domains of Flt-1. The amino acid sequence of Flt-1 (1338 amino acids), containing amino acids for the transmembrane and cytoplasmic domains, as well as the amino acid sequence of sFlt-1 (687 amino acids), are described in Genbank Accession No. P17948.

PlGF, as used herein, refers to placenta growth factor. PlGF has four currently recognized isotopes, including PlGF-1, PlGF-2, PlGF-3, and PlGF-4, which arise from alternative splicing. An example of a PlGF amino acid sequence (221 amino acids) and the PlGF-1 isoform amino acid sequence (149 amino acids) are described in Genbank Accession No. P49763.

sFlt-1 binds to PlGF, and the result is referred to herein as the sFlt-1:PlGF complex.

With these terms in mind, in one aspect the invention relates to a method of determining the presence or amount of sFlt-1:PlGF complex. The method comprises:

a) capturing the complex with capture agent that binds to PlGF, and detecting the complex with detector agent that binds to one or both of sFlt-1 and sFlt-1:PlGF complex; or b) capturing the complex with capture agent that binds to sFlt-1, and detecting the complex with detector agent that binds to one or both of PlGF and sFlt-1:PlGF complex; or c) capturing the complex with capture agent that binds to sFlt-1:PlGF complex, and detecting the complex with detector agent that binds to sFlt-1:PlGF complex, wherein capture agent and detector agent are capable of being bound simultaneously to the complex; or d) capturing the complex with capture agent that binds to sFlt-1:PlGF complex, and detecting the complex with detector agent that binds to one or both of PlGF and sFlt-1.

In another aspect, the invention relates to a method of guiding therapy of, or predicting, detecting, or monitoring, vascular, vascular-related, cancer, cancer-related, cardiac, cardiac-related, preeclampsia or preeclampsia-related disease in an individual. The method comprises:

a) determining the presence or amount of sFlt-1:PlGF complex in a sample from an individual; and b) i) comparing the result of the sFlt-1:PlGF determination with one or more reference values; or ii) converting the result of the sFlt-1:PlGF complex determination into one or more transformed results, using one or more mathematical operations or one or more algorithms, and comparing the sFlt-1:PlGF complex transformed results with one or more reference values;

thereby guiding therapy of, or predicting, detecting, or monitoring, the disease.

In one embodiment, the method may further comprise:

a) determining the presence or amount of one or more molecular entities in the sample; and b) i) comparing the result of the molecular entities determination and the result of the sFlt-1:PlGF complex determination with the one or more reference values; or ii) converting the result of the molecular entities determination and the result of the sFlt-1:PlGF complex determination into one or more transformed results, using one or more mathematical operations or one or more algorithms, and comparing the molecular entities transformed results and the sFlt-1:PlGF transformed results with the one or more reference values.

In yet another embodiment, the method may further comprise:

a) determining the values of one or more physical attributes of the individual; and b) i) comparing the physical attributes determination and the result of the molecular entities determination and the result of the sFlt-1:PlGF complex determination with the one or more reference values; or ii) converting the physical attributes determination and the result of the molecular entities determination and the result of the sFlt-1:PlGF complex determination into one or more transformed results, using one or more mathematical operations or one or more algorithms, and comparing the physical attributes transformed results and the molecular entities transformed results and the sFlt-1:PlGF transformed results with the one or more reference values.

In an additional embodiment, the method may comprise:

a) determining the values of one or more physical attributes of the individual; and b) i) comparing the physical attributes determination and the result of the sFlt-1:PlGF complex determination with the one or more reference values; or ii) converting the physical attributes determination and the result of the sFlt-1:PlGF complex determination into one or more transformed results, using one or more mathematical operations or one or more algorithms, and comparing the physical attributes transformed results and the sFlt-1:PlGF transformed results with the one or more reference values.

Extending the concept of the subject invention beyond the illustrated preferred embodiments, the invention can relate to a first molecular entity and a second molecular entity capable of binding to each other to form a molecular complex, wherein in the preferred embodiment sFlt-1 is an example of a first molecular entity and PlGF is an example of a second molecular entity. sFlt-1:PlGF complex is an example of a molecular complex. The subject invention is described in detail below in respect to certain preferred embodiments involving angiogenic receptor sFlt-1 and angiogenic factors PlGF and VEGF. These molecular entities are of particular interest in respect to preeclampsia and preeclampsia-related disease.

Immunoassays—General Discussion Applicable to the Subject Invention

Analytical assays comprising agents that bind specifically to a substance whose presence or amount is to be determined are typically referred to as binding assays. Immunoassays are generally thought of as binding assays that utilize antibodies or fragments of antibodies as capture agents and detector agents. Although the invention is described in reference to capture and detector antibodies, binding agents other than antibodies also are contemplated. Such binding agents, as in the case of capture and detector antibodies, bind specifically to a first molecular entity or second molecular entity involved in complex formation or to the complex comprising the first and second molecular entities.

Immunoassays can be categorized as competitive or non-competitive (sandwich) immunoassays. In a competitive immunoassay, a labeled form of the substance to be determined is placed in competition with the (unlabeled) native substance derived from a sample. The labeled form competes with the native substance for binding to a fixed amount of a capture antibody; the capture antibody being capable of binding to the labeled substance and the (unlabeled) native substance—though not simultaneously. Unknown concentrations of the substance derived from the sample are determined from detectable signal arising from the labeled form of the substance that is either bound to the capture antibody or from the labeled form of the substance that is free, i.e., not bound to the capture antibody.

In a non-competitive (sandwich) immunoassay, the substance to be determined is contacted with capture antibody and detector antibody, which antibodies typically bind to the substance at different epitopes or, in any case, are capable of being bound to the substance simultaneously. There can be multiple types of capture antibody that bind to different epitopes of the substance and/or multiple types of detector antibody that bind to different epitopes of the substance. Detector antibody is labeled and capture antibody typically is immobilized on a solid support or is capable of being immobilized thereon. Conventional labels include radioactive tags, enzymes, chromophores, fluorophores, stable free radicals and enzyme cofactors, inhibitors and allosteric effectors.

Immunoassay methods can be performed using any suitable format. They can be carried out in solution, in test devices where soluble and insoluble components can be separated, or in dry analytical elements. Such immunoassay formats include, for example, enzyme-linked immunosorbent assays (ELISA), immunometric assays, dot blot (also known as slot blot) assays, etc. The immunoassays can be heterogeneous or homogeneous. In heterogeneous immunoassays, bound components are separated from free, non-bound components—usually by way of one or more wash-steps. In homogeneous immunoassays, separation of bound from free components is not required.

Numerous publications relating to immunoassays and immunoassay methods are available ("Practical Immunoassay", Butt ed, Marcel Dekker, 1984; "Immunochemistry of Solid Phase-Immunoassay"; Butler, CRC Press, 1991; "Immunoassay", Law ed, Taylor & Francis, 1996; "Immunoassay", Eleftherios et al., Academic Press, 1996; "Principles and Practice of Immunoassay", Second Edition, Price and Newman eds, Macmillan, 1997; "Immunoassays in the Clinical Laboratory", Nakamura et al. eds, Alan R Liss, Inc, 1979; "Quantitative Enzyme Immunoassay", Engvall et al. eds, Blackwell Scientific Publications, 1978; Sommer et al., Clin Chem 32:1770-1774, 1986; "A Primer for Multilayer Immunoassay", Berke, American Chemical Society Conference Proceeding, p 303-312, Plenum Press, 1988; U.S. Pat. No. 4,200,690; U.S. Pat. No. 4,207,307; U.S. Pat. No. 4,407,943; U.S. Pat. No. 4,550,075; U.S. Pat. No. 4,551,426; U.S. Pat. No. 4,560,648; U.S. Pat. No. 5,312,744; U.S. Pat. No. 5,314,830; U.S. Pat. No. 5,424,220; U.S. Pat. No. 5,415,998; U.S. Pat. No. 5,501,949; U.S. Pat. No. 5,518,887; U.S. Pat. No. 5,663,054; U.S. Pat. No. 5,789,261; U.S. Pat. No. 5,935,780; U.S. Pat. No. 5,958,339; U.S. Pat. No. 6,087,188; U.S. Pat. No. 6,096,563; U.S. Pat. No. 6,121,006; U.S. Pat. No. 6,143,575; U.S. Pat. No. 6,395,503; U.S. Pat. No. 6,878,515; U.S. Pat. No. 6,838,250; U.S. Pat. No. 4,372,745; U.S. Pat. No. 4,670,381; U.S. Pat. No. 4,483,921; U.S. Pat. No. 4,517,288; U.S. Pat. No. 4,822,747; U.S. Pat. No. 4,824,778; U.S. Pat. No. 4,829,012; U.S. Pat. No. 4,839,299; U.S. Pat. No. 4,847,194; U.S. Pat. No. 4,847,195; U.S. Pat. No. 4,853,335; U.S. Pat. No. 4,855,226; U.S. Pat. No. 4,857,453; U.S. Pat. No. 4,857,454; U.S. Pat. No. 4,859,610; U.S. Pat. No. 4,863,876; U.S. Pat. No. 4,868,106; U.S. Pat. No. 4,868,130; U.S. Pat. No. 4,879,219; U.S. Pat. No. 5,776,933.

Details relating to dry analytical immunoassay elements may be found in the following publications and references cited therein: U.S. Pat. No. 3,867,258; U.S. Pat. No. 3,992,158; U.S. Pat. No. 4,042,435; U.S. Pat. No. 4,050,898; U.S. Pat. No. 4,066,403; U.S. Pat. No. 4,153,668; U.S. Pat. No. 4,258,001; U.S. Pat. No. 4,292,272; U.S. Pat. No. 4,430,436.

A support can be any material that is insoluble, or can be made insoluble by a subsequent reaction. The support can be chosen for its intrinsic ability to attract and immobilize a capture agent. Alternatively, the support can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the support and has the ability to immobilize the capture agent through a binding reaction. The linking agent enables the indirect binding of the capture agent to a support before the performance of the assay or during the performance of the assay. The support can be, for example, plastic, derivatized plastic, magnetic or non-magnetic metal, glass or silicon, including, for example, a test tube, microwell, microtiter well, membrane, sheet, bead, microparticle, chip, and other configurations known to those of ordinary skill in the art. A support can be porous or non-porous material that is insoluble or essentially insoluble in aqueous compositions. A support can exist in a wide range of different forms and configurations: vessel, tube, microtiter plate, sphere, microparticle, rod, strip, filter paper, chromatography paper, membrane, etc.

The methods of the present invention can be adapted for use in systems that utilize microparticle technology including automated and semi-automated systems wherein the solid support comprises a microparticle as described in U.S. Pat. No. 5,006,309 and U.S. Pat. No. 5,089,424.

In a preferred format, capture agent is linked to biotin and immobilized on the internal surface of a microwell by way of biotin binding to avidin, streptavidin, or other biotin-binding agent.

Numerous publications relating to binding of molecules to supports are available. For instance: U.S. Pat. No. 4,624,930; U.S. Pat. No. 5,061,640; U.S. Pat. No. 4,945,042; U.S. Pat. No. 4,885,255; U.S. Pat. No. 5,362,624; U.S. Pat. No. 5,277,589; U.S. Pat. No. 5,268,306; U.S. Pat. No. 5,376,557; U.S. Pat. No. 5,858,803, U.S. Pat. No. 5,126,241; U.S. Pat. No.

5,362,655; U.S. Pat. No. 5,437,981; U.S. Pat. No. 5,792,606; U.S. Pat. No. 5,863,740; U.S. Pat. No. 5,935,780; U.S. Pat. No. 6,391,571.

In heterogeneous immunoassays separation of free from bound components can be effected by passing suitable liquid wash solution across the support, filtering soluble, free components away from the support, immuno-precipitating free components, precipitation with substances such as polyethylene glycol or ammonium sulfate, magnetic separation or binding to a different support, and so on.

A detector agent can be directly detectable or indirectly detectable. It may comprise a label that is capable of emitting a signal directly or indirectly. Suitable labels are known in the art, and include, for example, horseradish peroxidase, alkaline phosphatase, fluorescent tags, detectable tracers, and so forth. A label may be a chemical entity that is capable of directly eliciting a detectable signal—usually an optical signal:absorbance, reflectance, luminescence, and fluorescence. A signal may be derived from radioactivity. It may be voltammetric or conductometric, etc. A directly detectable label that is intrinsically capable of producing a detectable signal may include organic and inorganic substances capable of fluorescence, or phosphorescence, such as but not limited to, fluorescein and derivatives thereof, N-(3-fluoranthyl)-maleimide, radionucleides, such as carbon 14, tritium, phosphorus 32; azo-oxo, azo-tetrazo, azine, oxazine, thiazine, quinoline, indamine, pyrone and pyrazolone dyes. In general, a label can be a chemical element, a compound, or protein.

A label that is detectable indirectly usually will require the presence of one or more additional substances for production of detectable signal. Such labels include enzymes that require the presence of a substrate(s), a co-factor(s), or a metal(s). For example, horseradish peroxidase is a label that requires an electron donor and an oxidizing agent in order to generate a signal: for example, luminol and hydrogen peroxide to generate chemiluminescence, or triarylimidazole and hydrogen peroxide to generate dye.

A capture and/or detector agent in reference to the preferred embodiments is an agent that is capable of binding with specificity to sFlt-1, VEGF, PlGF or complexes comprising sFlt-1 and angiogenic factor. In general, considering a first molecular entity and a second molecular entity capable of binding to form a complex comprising both molecular entities, capture agent or detector agent that is stated to bind or specifically bind to the first molecular entity, unless otherwise indicated, is capable of binding to free first molecular entity and to the first molecular entity when it is bound to the second molecular entity in the complex. Similarly, capture agent or detector agent that is stated to bind or specifically bind to the second molecular entity, unless otherwise indicated, is capable of binding to free second molecular entity and to the second molecular entity when it is bound to the first molecular entity in the complex. Capture agent or detector agent stated to bind to complex or specifically bind to complex does not bind or does not bind substantially to free first molecular entity or free second molecular entity.

Capture and detector agents include antibodies or fragments thereof, and chimeric antibodies comprising antibody fragments derived from different biological origins, such as human/mouse, mouse/goat, human/goat. They include non-antibody proteins and peptides, such as, angiogenic factors, angiogenic receptors, and non-protein binding agents. Monoclonal or polyclonal antibodies or combinations of monoclonal and polyclonal antibodies represent preferred capture and detector agents.

The term "sample" or "biological sample" includes any quantity of a substance from a living thing or formerly living thing. Such living things include, but are not limited to, humans, mice, monkeys, rats, rabbits, horses, and other animals. Samples include, but are not limited to, blood, serum, urine, tears, cells, organs, tissues, bone, bone marrow, lymph, lymph nodes, synovial tissue, chondrocytes, synovial macrophages, endothelial cells, and skin.

Molecular Complex—Capture and Detection Applicable to the Subject Invention

Various immunoassay embodiments will be described symbolically in reference to determination of molecular complex FP comprising molecular entity F and molecular entity P.

In one kind of immunoassay embodiment, FP can be captured using immobilized or immobilizable capture agent specific for F. Capture agent is capable of binding to free F and to F in complex FP. "Free" F means F that is not bound to P though it may be bound to other molecular entities. Detection is carried out using detector agent, preferably labeled with horseradish peroxidase, which detector agent specifically binds to P and is capable of binding to free P and to P in complex FP. Similarly, "free" P means P that is not bound to F though it may be bound to other molecular entities. In another immunoassay embodiment, detection is carried out using detector agent, preferably labeled with horseradish peroxidase, which detector agent binds specifically to complex FP and does not bind or does not bind substantially to either free F or free P.

In an analogous immunoassay embodiment, FP can be captured using immobilized or immobilizable capture agent specific for P. Capture agent is capable of binding to free P and to P in complex FP. Detection is carried out using detector agent specific for F, which detector agent is capable of binding to free F and to F in complex FP. Or, detection is carried out using detector agent specific for complex FP, which detector agent does not bind or does not bind substantially to either free F or free P.

In another immunoassay embodiment, complex FP can be captured using immobilized or immobilizable capture agent that binds to complex FP, which capture agent does not bind or does not bind substantially to either free F or free P. Detection is carried out using detector agent also specific for complex FP, which detector agent does not bind or does not bind substantially to either free F or free P. In this embodiment capture and detector agent bind to different sites of complex FP or, in any case, are capable of being bound simultaneously to complex FP. Alternatively, detection can be carried out using detector agent specific for F, which detector agent is capable of binding to free F and to F in complex FP. Or, detection can be carried out using detector agent specific for P, which detector agent is capable of binding to free P and to P in complex FP. Or, detection can be carried out using detector agent specific for F (and capable of binding to free F and to F in complex FP) and detector agent specific for P (and capable of binding to free P and to P in complex FP).

In the above-described immunoassay embodiments, separation of non-bound from bound components is carried out where separation is desirable or necessary. For example, in the case where FP is captured using immobilized capture agent specific for F and capable of binding to free F and complex FP (thus capturing and immobilizing free F and complex FP) and wherein FP is detected using detector agent specific for P, which detector agent is capable of binding to free P and to complex FP, subsequent to capture, separation of bound components from non-bound components would be carried out—usually via a wash procedure. Thus, bound free F and bound FP are separated from non-bound free F, non-bound FP, and free P (P is not captured and therefore it is not bound). Detector agent is then introduced for binding to captured and immobilized complex FP without interference from free P—which is removed during the wash procedure.

Examples of antibodies which can be used for capture and detection of sFlt-1:PlGF complex include, but are not limited to: mouse monoclonal anti-sFlt-1 antibody RD-1-49560 (R&D Systems), 3661-M16 (R&D Systems) and 4449-M24 (R&D Systems); mouse monoclonal anti-sFlt-1 antibody RD-7-49566 (R&D Systems), mouse monoclonal anti-sFlt-1 antibody M14 (Ortho-Clinical Diagnostics), mouse monoclonal anti-PlGF antibody 37203 (R&D Systems), rat monoclonal anti-PlGF antibody 358932 (R&D Systems), rat monoclonal anti-PlGF antibody 358905 (R&D Systems), monoclonal antibody 358932 (R&D Systems) and 261 (Ortho Clinical Diagnostics).

In accordance with the subject invention, a composition is also provided for use in the immunoassay embodiments, i.e. for determining the presence or amount of sFlt-1:PlGF complex. The composition comprises:

a) capture agent that binds to PlGF and detector agent that binds to one or both of sFlt-1 and sFlt-1:PlGF complex; or b) capture agent that binds to sFlt-1 and detector agent that binds to one or both of PlGF and sFlt-1:PlGF complex; or c) capture agent that binds to sFlt-1:PlGF complex and detector agent that binds to sFlt-1:PlGF complex, wherein capture agent and detector agent are capable of being bound simultaneously to the complex; or d) capture agent that binds to sFlt-1:PlGF complex and detector agent that binds to one or both of PlGF and sFlt-1.

As in the methods of the subject invention, one or both of the capture and detector agents can be polyclonal antibodies, or one or both of the capture and detector agents can be monoclonal antibodies, or one or both of the capture and detector agents can be a combination of monoclonal and polyclonal antibodies.

Assay Calibration and Performance Verification Applicable to the Subject Invention Immunoassays require calibration and/or verification that the target analyte is detected with specified precision and accuracy. In respect to an immunoassay for determining complex FP, compositions comprising a purified form of the molecular complex FP can be used for such purposes. In the context of the present invention the term "purified" means that complex FP is or has been separated from free F and free P. Separation of complex FP from free F and free P can be achieved using one or more well known methods such as: methods that rely on the affinity of the individual components for specific binding partners, for example, F binding to (preferably immobilized) P, P binding to (preferably immobilized) F, or binding of the individual components to other binding partners such as F binding to (preferably immobilized) anti-F antibody, P binding to (preferably immobilized) anti-P antibody, or FP binding to (preferably immobilized) anti-FP antibody, or binding of the individual components to other types of specific binding partners (affinity chromatography); or, by way of ion exchange chromatography, metal-ion exchange chromatography, ligand exchange chromatography, or hydrophobic chromatography; or, using methods that rely on differences in mass and/or size and/or differences in net electric charge of the complex and its component molecular entities. These include size-exclusion chromatographic methods, centrifugation methods, molecular sieving methods, for example, membrane filtration, and electrophoretic methods, and so on.

If the complex is stable during separation and subsequent introduction into a storage composition (typically a liquid formulation)—wherein stable means that it does not readily dissociate to form substantial amounts of free F and free P during these procedures—the composition comprising the complex can then be placed under suitable conditions to maintain stability over longer times. It can, for example, be stored at a low temperature less than or equal to about 4° C. if it is in a liquid state, or the liquid composition can be frozen and maintained as a solid at a temperature below 0° C., or it can be lyophilized and maintained in a state at some appropriate temperature which could even be greater than about 20° C. Upon removal from storage, after having been thawed or reconstituted if necessary, it should be stable for an acceptable period of time under the conditions for which it will be used for assay calibration or verification.

Modified forms of the complex can be produced in which F and P are covalently bonded to each other (for example, sFlt-1 covalently bonded to PlGF). Such a covalently modified form of FP will be stable with respect to dissociation to form free F and free P. Preferably, modified, covalent complex FP and noncovalent complex FP have substantially the same or similar binding properties with respect to capture agent and detector agent. If a modified, covalent form of FP and unmodified, noncovalent form, or natural/native form of complex FP do not have substantially the same or sufficiently similar binding properties with respect to capture a d detector agent, appropriate mathematical correction can be applied to compensate for the differences in binding properties, as is known in the analytical arts. In the context of the present invention the term "form" of FP shall be understood to include intact, noncovalent, natural/native FP purified/isolated from a suitable source (such as human serum, placental tissue or fluids, and so on), noncovalent FP prepared from native F and native P or native F and recombinant P or recombinant F and recombinant P and, modified, covalently bonded FP (F and P covalently bonded to each other) prepared from native F and native P or native F and recombinant P or recombinant F and recombinant P.

In accordance with this aspect of the subject invention, a composition is also provided which comprises a purified form of sFlt-1:PlGF complex. One or both of sFlt-1 and PlGF of the sFlt-1:PlGF complex may be native, or one or both of sFlt-1 and PlGF of the sFlt-1:PlGF complex may be recombinant.

Predicting, Detecting/Diagnosing, Monitoring Disease Applicable to the Subject Invention It is conventional practice to determine the presence or amount of a single substance (marker/biomarker) in a biological sample of an individual in order to determine if the individual is afflicted with a particular disease (detecting/diagnosing), is likely to become afflicted (predicting), to determine progression of the disease (monitoring), or if the individual is responding to treatment (monitoring).

For example, determining the presence of glucose (qualitative assay) or the amount of glucose (quantitative assay) in a urine or serum sample of an individual often is carried out in order to confirm a diagnosis of diabetes or to monitor the efficacy of treatment of an individual diagnosed as diabetic. An optical signal—oftentimes a calorimetric signal in both qualitative and quantitative assays—will form in proportion to the amount of glucose in a sample. In one type of calorimetric assay, the amount or color intensity of dye that forms, dye density, can be determined visually in a qualitative manner. Alternatively, the amount or color intensity of dye can be determined more accurately and precisely using suitable instrumentation to measure and assign a numeric value to the dye density. Visually determined dye density produced with a biological sample of an individual is usually compared with a reference dye density scale or dye density range comprising a scale or range of dye densities correlated with non-diabetics and diabetics. Quantified dye density is usually compared with a numeric reference value or numeric reference range of values similarly correlated.

Reference values or reference ranges with respect to a particular disease are typically derived from populations diagnosed as free of that particular disease (normal) and populations diagnosed as afflicted with that particular disease. The reference values or reference ranges can include values or measures associated with different stages of the disease. Sample derived results can be compared with these reference values or reference ranges and the disease thereby detected/diagnosed or monitored. In the case of multiple biomarkers alone or in conjunction with physical attributes (discussed below), reference values and reference value ranges can also be correlated with different forms, origins, causes, and so forth, of a disease, which forms, origins, causes, etc. are responsive to different therapies. Sample derived results can be compared with these reference values or reference ranges and therapy to treat an individual can thereby be informed or guided.

The terms "reference value", "reference range of values", and so forth, if not otherwise indicated, are intended to encompass quantitative or numeric reference population measures and qualitative or visual reference population measures, such as dye density scales, color or hue scales, and so forth.

The conventional practice of using a single biomarker for detecting and monitoring a disease has been and continues to be a valuable aid to clinicians and the patients they serve. Frequently, more than one biomarker is known to be associated with a disease. For example, glycosylated hemoglobin is also associated with diabetes. Determining the amount of glucose and glycosylated hemoglobin in a sample from an individual diagnosed as diabetic can provide more information about the state of the disease in the individual or the effect of treatment than either determination alone. The determination of multiple biomarkers not only improves diagnosis and monitoring of a disease but, it may also enable a clinician to determine the likelihood or probability that an individual will be afflicted with a disease or is in a stage of the disease where clinical evaluation is uninformative. The determination of multiple biomarkers can also be useful in guiding therapy—allowing a clinician to distinguish different forms or stages of a disease so as to permit treatment of an individual using appropriate therapeutic measures. The determination of multiple biomarkers can be used in conjunction with one or more physical attribute of the individual to further improve predictive utility, diagnostic utility, and selection of appropriate therapy.

Such additional multiple biomarkers are referred to herein as one or more molecular entities. In the case of sFlt-1:PlGF complex detection, such molecular entities include, but are not limited to, endoglin, soluble endoglin, creatinine, c-reactive protein, urine protein, placental protein 13, human chorionic gonadotropin hormone, or alpha-fetoprotein and liver enzymes, such as, aspartate aminotransferase, alanine aminotransferase, alkaline phosphatase and gamma-glutamyl transferase. As used herein, VEGF can include $VEGF_{121}$, $VEGF_{145}$, $VEGF_{165}$, $VEGF_{165b}$, $VEGF_{167}$, $VEGF_{183}$, $VEGF_{186}$, $VEGF_{189}$, or $VEGF_{206}$.

In a presently preferred embodiment, sFlt-1:PlGF complex is detected and the disease is preeclampsia or preeclampsia-related and guiding therapy, predicting, detecting, or monitoring is within the first 15 weeks of gestation or within the first 20 weeks of gestation or within the first 30 or more weeks of gestation.

Mathematical operations and algorithms can be used to convert the amounts of two or more biomarkers into one or more transformed-results. Such mathematical operations can include computing a ratio of the molecular entities determination to the sFlt-1:PlGF complex determination or the sFlt-1:PlGF complex determination to the molecular entities determination. The transformed-result or -results can be more informative than the direct concentration-based results. Mathematical operations or algorithms that convert the determinations of one or more biomarkers in combination with one or more physical attributes of an individual into one or more transformed-results also are being employed to provide improvements in guiding therapy, predicting, detecting/diagnosing, and monitoring disease. Physical attributes include, but are not limited to: gestational age, race, gender, age, blood pressure and body mass index. These can be used individually or in any combination along with one or more biomarker.

Numerous patent and non-patent publications are available describing mathematical operations and algorithms and their use in clinical diagnostics. For example, US Patent Application Publ No 2006/381104, US Patent Application Publ No 2003/700672, US Patent Application Publ No 2003/410572, US Patent Application Publ No 2003/634145, US Patent Application Publ No 2005/323460, PCT Intl Publ No WO 2007/044860, US Patent Application Publ No 2002/330696, US Patent Application Publ No 2002/331127, US Patent Application Publ No 1997/912133, U.S. Pat. No. 6,306,087, U.S. Pat. No. 6,248,063 and U.S. Pat. No. 5,769,074.

Example I

Assay for sFlt-1:PlGF Complex

In this Example an immunometric assay is described for determining the amount of sFlt-1:PlGF complex in a sample, and the utility of the sFlt-1:PlGF complex as a diagnostic indicator of preeclampsia is shown.

Figure 1:
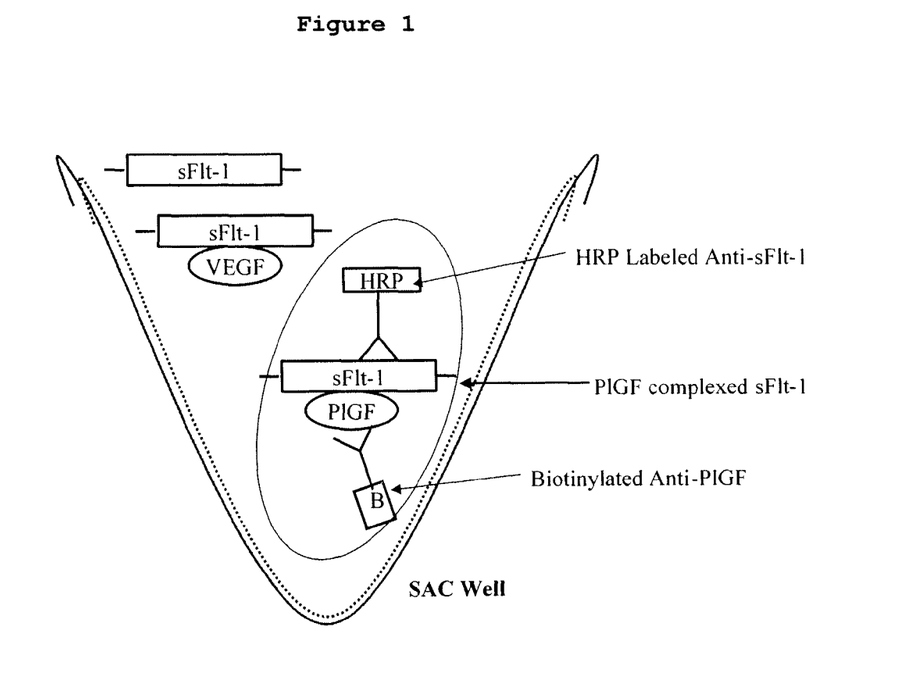
FIG. 1 illustrates an assay structure for determining sFlt-1:PlGF complex by way of PlGF capture and sFlt-1 detection.

The immunoassay format depicted in FIG. 1 was used to capture and detect sFlt-1:PlGF complex. sFlt-1:PlGF complex in a sample is captured using biotinylated rat anti-PlGF antibody. sFlt-1:PlGF complex captured by anti-PlGF antibody is immobilized by way of biotin binding to streptavidin coated on the surface of a reaction vessel. Free sFlt-1 and sFlt-1:VEGF complex are not captured by biotinylated anti- PlGF capture agent and are removed along with other non-bound substances during a wash procedure. The complex is detected by way of luminescence using horseradish peroxidase (HRP)-labeled anti-sFlt-1 antibody. The luminescence signal generated from bound HRP-labeled anti-sFlt-1 antibody is directly proportional to the concentration of sFlt-1: PlGF present in the sample. Any free PlGF captured by the biotinylated anti-PlGF capture agent does not form a sandwich with the HRP-labeled anti-sFlt-1 antibody and is not measured.

Materials used in the immunoassay include:

1. Biotin Reagent: biotinylated anti-PlGF antibody at 2.25 µg/mL in a pH buffered aqueous composition. Biotinylated anti-PlGF antibodies capable of binding to sFlt-1:PlGF complex include but are not limited to Ortho-Clinical Diagnostic's mouse monoclonal antibody OCD-261 and rat monoclonal antibodies 358905 and 358932 available from R&D Systems, Minneapolis, Minn.

2. Conjugate Reagent: HRP-labeled anti-sFlt-1 antibody at 1.125 µg/mL in a pH buffered aqueous composition. HRP-labeled anti-sFlt-1 antibodies which do not interfere with binding of VEGF or PlGF to sFlt-1 include but are not limited to Ortho-Clinical Diagnostic's mouse monoclonal antibody clones 3661-M16 and 4449-M24 and R&D System's monoclonal antibody 49560.

3. Calibrators were prepared by adding purified sFlt-1: PlGF complex to horse serum (where "purified sFlt-1:PlGF complex" means, as noted above, the complex is or has been separated from free sFlt-1 and free PlGF). Ten fold molar excess of recombinant human PlGF obtained from R&D Systems (Catalog Number: 264-PG) was incubated for 20 min at 20° C. followed by an overnight incubation at 2-8° C. with full length sFlt-1 (687 amino acids) obtained from Scios (Scios Inc., Mountain View, Calif.) in phosphate buffered saline (PBS) buffer pH 7.4. The sFlt-1:PlGF complex was separated from free PlGF by size exclusion chromatography on a SUPERDEX® 200 column equilibrated with phosphate buffer containing 0.25M ethanolamine at pH 8.5. The fractions containing the complex were pooled and concentrated using a centrifugal concentration unit. The concentrated pool of complex was then dialyzed into PBS pH 7.4.

The purified sFlt-1:PlGF complex was diluted to obtain different concentrations in horse serum (GIBCO, Catalog number 26050) to provide calibrators CR1 to CR10 spanning an sFlt-1:PlGF complex concentration range between 0.0 and 25,000 µg/mL.

4. Reaction vessels were streptavidin-coated microwells (SAC wells).

Immunoassay Protocol

The immunoassay protocol was as follows:

Sample (80 µL) was combined with 80 µL Biotin Reagent in a SAC well and the mixture was incubated for 21 minutes at 37° C. A wash-step using VITROS® ECi Universal Wash Reagent followed the incubation. After the wash-step, Conjugate Reagent (160 µL) was added to the SAC well and incubated for 21 minutes at 37° C. A second wash-step using the VITROS® ECi Universal Wash Reagent followed the incubation. VITROS® ECi Signal reagent comprising luminescence reagents was then introduced and incubated for 5 minutes. The luminescence signal was acquired following the incubation.

Figure 2:
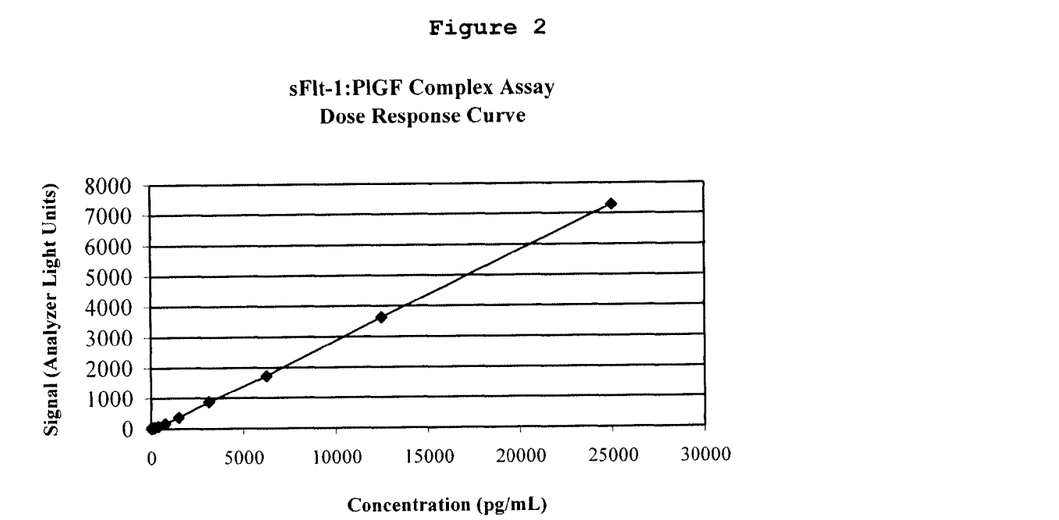
FIG. 2 shows a dose response curve for an sFlt-1:PlGF-1 complex assay.

The analytical and clinical performance of the sFlt-1:PlGF complex assay was evaluated. Results are shown in Tables 1-6 and FIGS. 2-4. In Table 1 the signal responses, Analyzer Light Units (ALU), obtained using calibrator fluids (comprising sFlt-1:PlGF complex) are shown. The data from Table 1 is shown as a dose-response plot in FIG. 2. Evidence confirming that only sFlt-1:PlGF complex (and not free sFlt-1 or free PlGF) was detected in the assay was provided by way of cross reactivity studies in which samples comprising different concentrations of free sFlt-1 or free PlGF (and no sFlt-1:PlGF complex) were used in place of samples comprising sFlt-1:PlGF complex in the assay. These results are presented in Tables 2 and 3 where it can be seen that free sFlt-1 and free PlGF do not register significant responses.

Figure 3:
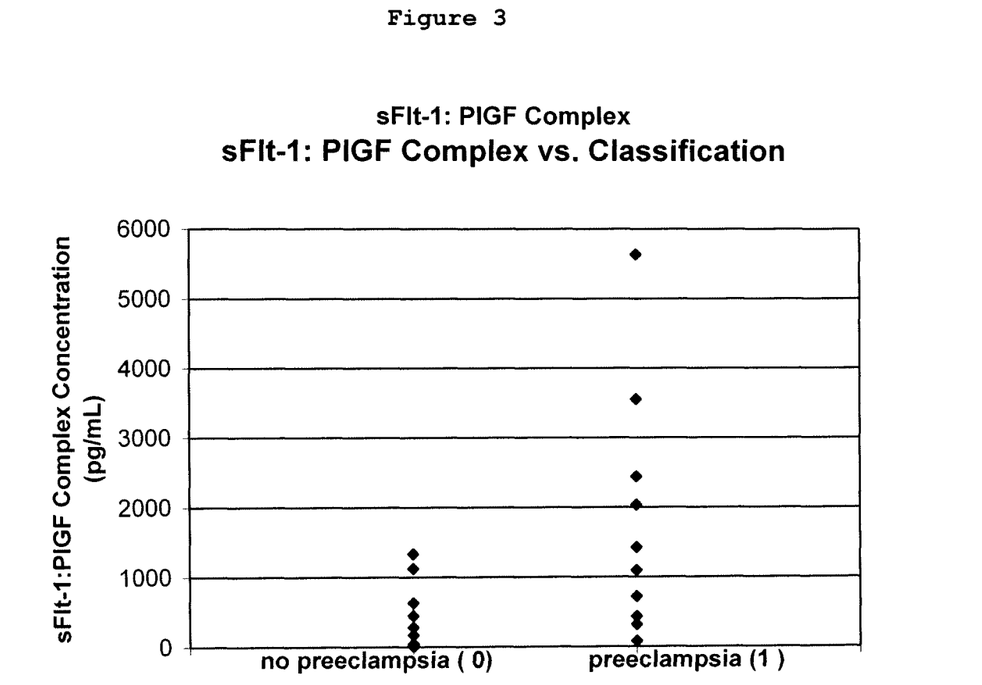
FIG. 3 shows a dot-plot of normal (0) and preeclampsia (1) patient sample results based on an sFlt-1:PlGF-1 complex assay.

Serum samples obtained from women in the 2nd or 3rd trimester of pregnancy diagnosed as either having preeclampsia or not having preeclampsia (normal) were assayed for sFlt-1:PlGF complex using the above-described assay. The results are summarized in Table 4. A dot-plot of the results is shown in FIG. 3 where it can be seen that the sFlt-1:PlGF complex concentrations found in the serum samples from the normal population are generally lower and clearly discriminated from the concentrations found in the serum samples from the population diagnosed as having preeclampsia. Receiver operating characteristic (ROC) analysis of the data was carried out. The area under ROC curve (Table 5) is 0.783 demonstrating that the sFlt-1:PlGF complex is a useful biomarker for detecting/diagnosing preeclampsia.

Figure 4:
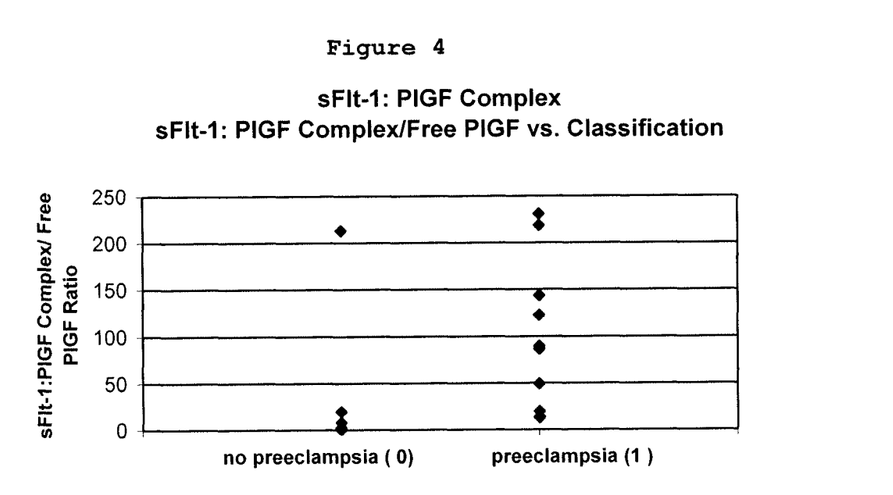
FIG. 4 shows a dot-plot of the computed ratios of sFlt-1:PlGF complex to free PlGF in samples from normal (0) and preeclampsia (1) patients.

For each sample, the ratio of the amount of sFlt-1:PlGF complex present in a sample relative to the amount of free PlGF present in the sample was computed and compared with the amount of free PlGF as determined using a free PlGF assay. These results are provided in Table 4. A dot-plot of the ratio (sFlt-1:PlGF complex/free PlGF) for each sample versus clinical diagnosis is shown in FIG. 4. The computed ratios for the normal population samples are generally smaller in magnitude and clearly discriminated from the computed ratios for the preeclampsia population samples. The area under ROC curve (Table 6) is 0.889 demonstrating that the ratio, sFlt-1:PlGF complex/free PlGF, is also a useful marker for preeclampsia.

Example II

ELISA Detection of sFlt-1:PlGF Complex Using Anti-sFlt-1 Capture

The use of ELISA methods for determining sFlt-1:PlGF complex is described in this Example. In this assay method, free sFlt-1 and sFlt-1:PlGF complex are captured using anti-sFlt-1 antibody, and labeled anti-PlGF antibody is used to detect sFlt-1:PlGF complex.

Plate Coating

Costar 96-well microtiter high-binding plates were coated with 100 µL/well of a 10 mM phosphate, 2 mM EDTA, pH 7.0 solution containing 1 ng/mL of anti-sFlt-1 antibody 49560 (R&D Systems) and incubated for 18 hrs at 25° C. Wells were washed once (PBS with 0.05% TWEEN®-20), followed by addition of 290 µL/well of blocking buffer (1% bovine serum albumin in phosphate buffered saline, pH 7.0), then incubated for 1 hr at 25° C. Wells were aspirated and dried for 4 hrs in a low humidity incubator then sealed in air-tight bags prior to use.

ELISA Method

A series of samples containing a constant amount of recombinant sFlt-1 (purified recombinant sFlt-1, Scios;

expressed in insect cells; corresponding to the 687 amino acid full-length soluble fms-like tyrosine kinase 1) and varying amounts of recombinant PlGF (149 amino acids; PlGF-1; expressed in *E. coli*; R&D Systems, Catalog Number: 264-PG/CF) were incubated together in sample diluent (blocker casein in PBS with 0.05% TWEEN®-20, Pierce) to allow formation of a sFlt-1:PlGF complex. 100 µL of each pre-incubated sample was added to a microtiter well. 100 µL sample diluent was added to at least one well to serve as control. Wells were incubated for 15 minutes at 37° C. with shaking. Non-bound substances were removed by washing the plate 6 times with wash buffer (PBS with 0.05% TWEEN®-20). Total sFlt-1, free sFlt-1 and sFlt-1:PlGF complex were measured individually in anti-sFlt-1 antibody coated plates by addition of 100 µL/well of specific HRP-labeled antibodies (1 µg/mL in blocker casein in PBS with 0.05% TWEEN® 20) as outlined in Table 7. After addition of each detector antibody, the plate was incubated for 15 minutes with shaking at 37° C. The plate was washed six times with wash buffer. 10 µL of O-Phenylenediamine (OPD) substrate reagent was added to each well and incubated in the dark for 30 minutes at 25° C. 25 µL stop solution was added to each well and the absorbance at 492 nm was obtained. (HRP substrate, OPD reagent and stop solution were from Ortho-Clinical Diagnostics, Inc., Raritan, N.J., USA).

ELISA Results—Total sFlt-1

The absorbance at 492 nm obtained with each sample is provided in Table 8. HRP-labeled anti-sFlt-1 antibody M14 (Ortho-Clinical Diagnostics) binds to both free sFlt-1 and sFlt-1:PlGF complex, therefore, free sFlt-1 and sFlt-1 in the sFlt-1:PlGF complex are detected. As shown in Table 8, the signal response for total sFlt-1 (sum of observed signals for free sFlt-1 and sFlt-1:PlGF complex) is constant, independent of PlGF concentration.

ELISA Results—Free sFlt-1

HRP-labeled anti-sFlt-1 antibody 49566, (R&D Systems) binds to free sFlt-1 and does not bind sFlt-1:PlGF complex, therefore, only free sFlt-1 is detected. A decrease in signal response is observed as the PlGF concentration increases from 0 to 2000 pg/mL (Table 8). This is expected: as PlGF concentration increases more sFlt-1:PlGF complex forms and the concentration of free sFlt-1 decreases.

ELISA Results—sFlt-1:PlGF Complex

HRP-labeled anti-PlGF antibody 358905 (R&D Systems) binds to PlGF and therefore only sFlt-1 bound in complex sFlt-1:PlGF is detected. Table 8 shows an increase in signal response as the PlGF concentration increases from 0 to 2000 pg/mL.

These results as provided in Table 8 demonstrate that total sFlt-1, free sFlt-1 and sFlt-1:PlGF complex can be measured in an ELISA format using anti-sFlt-1 antibodies to capture the molecular species comprising sFlt-1.

The presence or amount of sFlt-1:PlGF complex in a sample can be determined by capture of sFlt-1 and detection of PlGF as demonstrated, and the measurement so obtained, alone or in conjunction with additional chemical and/or physical biomarkers, can be used as a diagnostic indicator for preeclampsia.

ELISA Detection of sFlt-1:PlGF Complex Using Anti-PlGF Capture

In another ELISA method, free PlGF and sFlt-1:PlGF complex are captured using anti-PlGF antibody. Labeled anti-sFlt-1 antibody is used to detect sFlt-1:PlGF complex.

Plate Coating

Costar 96-well microtiter high-binding plates were coated with 100 µL/well of a 10 mM phosphate, 2 mM EDTA, pH 7.0 solution containing 0.8 µg/mL of anti-PlGF antibody 358932 (R&D Systems) and incubated 18 hrs at 25° C. Wells were washed once (PBS with 0.05% Tween®-20), followed by addition of 290 µL/well of blocking buffer (1% bovine serum albumin in phosphate buffered saline, pH 7.0), then incubated for 1 hr at 25° C. Wells were aspirated and dried for 4 hrs in a low humidity incubator, then sealed in air-tight bags prior to use.

ELISA Method

A series of samples as shown in Table 9, contain a constant amount of recombinant PlGF (SEQ ID NO:2; expressed in *E. coli*; R&D Systems, Catalog Number: 264-PG/CF) and varying amounts of recombinant sFlt-1 (687 amino acid full-length soluble fms-like tyrosine kinase 1; expressed in insect cells; Scios, Inc.) in a sample diluent (Blocker Casein in PBS with 0.05% TWEEN®-20, Pierce) which are incubated together to allow formation of a sFlt-1:PlGF complex; the mixture is added to the coated wells and the plate is incubated with shaking at 37° C. for 15 minutes. Non-bound substances are removed by washing the plate with a mild detergent based buffer. Total PlGF, free PlGF and sFlt-1:PlGF complex are measured individually in anti-PlGF antibody coated plates by addition of 100 µL/well of specific HRP-labeled antibodies (1 µg/mL in Blocker Casein in PBS with 0.05% TWEEN®-20, Pierce) as outlined in Table 7. After addition of each detector antibody the plate is incubated for 15 minutes with shaking at 37° C. The plate is washed six times with wash buffer. A colorimetric reaction follows addition of 100 µL/well of OPD HRP substrate reagent and incubation in the dark for 30 minutes at 25° C. 25 µL/well stop solution is added and the absorbance at 492 nm is obtained. (HRP substrate O-Phenylenediamine reagent and stop solution were from Ortho-Clinical Diagnostics, Inc., Raritan, N.J., USA).

ELISA Results—Total PlGF

Table 9 lists the absorbance at 492 nm for each sample following each specific reaction. HRP-labeled anti-PlGF antibody 358905 (R&D Systems) binds to both free PlGF and sFlt-1:PlGF complex, therefore, free PlGF and PlGF in the sFlt-1:PlGF complex are detected. The total PlGF response column in Table 9 shows a constant response for samples with a PlGF concentration of 2000 pg/mL, regardless of the concentration of sFlt-1.

ELISA Results—Free PlGF

HRP-labeled anti-PlGF antibody 37203 (R&D Systems) binds to free PlGF and does not bind sFlt-1:PlGF complex, therefore, only free PlGF is detected. Table 9 shows a decrease in signal response as the sFlt-1 concentration increases from 0 to 2000 pg/mL. The concentration of free PlGF molecules should decrease and the concentration of sFlt-1:PlGF complex should increase as free PlGF binds to sFlt-1.

ELISA Results—sFlt-1:PlGF Complex

HRP-labeled anti-sFlt-1 antibody M14 (Ortho-Clinical Diagnostics) binds to sFlt-1 and to sFlt-1:PlGF complex and therefore only PlGF captured as a sFlt-1:PlGF complex is detected. Table 9 shows an increase in signal response as the sFlt-1 concentration increases from 0 to 2000 pg/mL.

The results outlined in Table 9 demonstrate total PlGF, free PlGF and the sFlt-1:PlGF complex can be measured in an ELISA format using anti-PlGF antibodies to capture all PlGF species and to independently detect each. As increasing concentrations of sFlt-1 is added to a constant concentration of PlGF, the free PlGF response is decreased and the sFlt-1:PlGF complex response is increased as demonstrated by the change in absorbance at 492 nm.

The presence or amount of sFlt-1:PlGF complex in a sample can be determined by capture of PlGF and detection of sFlt-1 as demonstrated, and the measurement so obtained, alone or in conjunction with additional chemical and/or physical biomarkers, can be used as a diagnostic indicator for preeclampsia.

Example III sFlt-1:PlGF Complex, Total sFlt-1, Free PlGF Gestation Age

Weeks 27-37

Total sFlt-1 and Free PlGF Assays

Assays of total sFlt-1 and free PlGF were carried out using R&D Systems QUANTIKINE® Kits Catalog Nos. DVR100B and DPG00, respectively. The assays were conducted according to protocols described in the R&D Systems package inserts for these products.

sFlt-1:PlGF Complex Assay

As in Example I, the immunoassay format depicted in FIG. 1 was used to capture and detect sFlt-1:PlGF complex.

Materials used in the immunoassay include:

1. Biotin Reagent: biotinylated anti-PlGF antibody (Ortho Clinical Diagnostics mouse monoclonal, OCD-261) at 6.0 μg/mL in a pH buffered aqueous composition. Other biotinylated anti-PlGF antibodies capable of binding to sFlt-1:PlGF complex are available from R&D Systems, Minneapolis, Minn.

2. Conjugate Reagent: HRP-labeled anti-sFlt-1 antibody at 4.5 μg/mL in a pH buffered aqueous composition. HRP-labeled anti-sFlt-1 antibodies which do not interfere with binding of VEGF or PlGF to sFlt-1 include but are not limited to Ortho-Clinical Diagnostic's mouse monoclonal antibody clones 3661-M16 and 4449-M24 and R&D Systems monoclonal 49560.

3. Calibrators were prepared by adding purified sFlt-1:PlGF complex to horse serum (where "purified sFlt-1:PlGF complex" means, as noted above, the complex is or has been separated from free sFlt-1 and free PlGF). Ten fold molar excess of recombinant human PlGF obtained from R&D systems (Catalog Number: 264-PG) was incubated for 20 min at 20° C. followed by an overnight incubation at 2-8° C. with full length sFlt-1 (687 amino acids) (Scios Inc., Mountain View, Calif. USA) in PBS buffer pH 7.4. The sFlt-1:PlGF complex was separated from free PlGF by size exclusion chromatography on a SUPERDEX® 200 column equilibrated with phosphate buffer containing 0.25M ethanolamine at pH 8.5. The fractions containing the complex were pooled and concentrated using a centrifugal concentration unit. The concentrated pool of complex was then dialyzed into PBS pH 7.4.

The purified sFlt-1:PlGF complex was diluted at different concentrations in horse serum (GIBCO, Catalog number 26050) to generate Calibrators CR1 to CR10 spanning sFlt-1 Complex concentration of 0.0 to 25,000 pg/mL.

4. Reaction vessels were streptavidin-coated microwells (SAC wells).

Immunoassay Protocol

The immunoassay protocol was as follows:

Sample (80 μL) was combined with 35 μL Biotin Reagent and 35 μL Conjugate Reagent in a SAC well and the mixture was incubated for 21 minutes at 37° C. A wash-step using VITROS® ECi Universal Wash Reagent followed the incubation. After the wash-step VITROS® ECi Signal Reagent was then introduced and incubated for 5 minutes. The luminescence signal was acquired following the incubation.

Each patient sample was assayed in duplicate for PlGF-1 and sFlt-1 according to R&D Systems ELISA assay protocols. A single assay of each patient sample for sFlt-1:PlGF-1 complex was carried out using the sFlt-1:PlGF-1 complex assay procedure as described above. The mean of the R&D System assay duplicates and the sFlt-1:PlGF-1 complex assay results for each patient sample are reported in the top portion of Table 10. Gestational age at the time of sample collection is reported in column 2 of Table 10. Diagnoses established near the time of sample collection according to the American College of Obstetrics and Gynecology (ACOG) guidelines are reported in column 3. Areas under ROC curves were determined as provided in the bottom portion of Table 10: PlGF-1 assay (0.8796), sFlt-1 assay (0.7994), sFlt-1:PlGF complex assay (0.7654), sFlt-1/PlGF ratio (0.8519) and sFlt-1:PlGF complex/PlGF ratio (0.8642). These data show that for gestational age 27 to 37.4, the clinical performance of sFlt-1:PlGF Complex assay on its own or as a ratio to free PlGF assay is comparable to that of an assay which measures total sFlt-1.

Example IV sFlt-1:PlGF Complex, sFlt-1, PlGF Gestation Age

Weeks 13-21

As evidenced in this Example, evaluation of the presence or amount of sFlt-1:angiogenic factor complex provides superior clinical utility for diagnosis and prediction of preeclampsia compared with total sFlt-1 or the ratio of total sFlt-1 to free PlGF in early stages of gestation. Similarly, the ratio of sFlt-1:PlGF complex to free PlGF has superior clinical utility for diagnosis and prediction of preeclampsia compared with free PlGF, total sFlt-1 or the ratio of total sFlt-1 to free PlGF.

As in Example III, each patient sample was assayed in duplicate for free PlGF and total sFlt-1 according to R&D Systems ELISA assay protocols and a single assay was carried out on each patient sample for sFlt-1:PlGF complex using the complex assay procedure. The results are shown in Table 11. Gestational age at the time of sample collection is reported in column 2 of Table 11. Diagnoses were established according to the ACOG guidelines and assignments of mild and severe preeclampsia were rendered based on ICD-9 code designations. These are listed in columns 3 and 4 of Table 11. Upon collection, the blood samples were archived for later assay; diagnoses having been made between weeks 21 and post partum.

Areas under ROC curves were determined as provided in Table 12. The results presented in the uppermost data panel (Mild or Severe PE) are based on 94 patient samples collected within weeks 13-21 of gestation. The diagnoses of mild and severe preeclampsia were grouped together as preeclampsia-positive during ROC analysis. The computed areas under the ROC curves follow: free PlGF assay (0.5745), total sFlt-1 assay (0.5029), sFlt-1:PlGF complex assay (0.6331), total sFlt-1/free PlGF ratio (0.5396) and sFlt-1:PlGF complex/free PlGF ratio (0.6392). These results indicate that total sFlt-1, free PlGF and the total sFlt-1/free PlGF ratio are not useful for predicting or detecting preeclampsia during early stages of gestation. However, the sFlt-1:PlGF complex and sFlt-1:PlGF complex/free PlGF ratio results suggest that they are clinically capable of discriminating between subjects who subsequently developed mild or severe preeclampsia from those who did not.

The results presented in the middle data panel (Severe PE, Mild PE=Normal) are based on the same 94 patient samples; however, during ROC analysis the diagnoses of mild preeclampsia were reclassified as normal. Areas under the ROC curves are as follows: free PlGF assay (0.7142), total sFlt-1 assay (0.5622), sFlt-1:PlGF complex assay (0.6942), total sFlt-1/free PlGF ratio (0.6771) and sFlt-1:PlGF complex/free PlGF ratio (0.7445). These results indicate the superior clinical capability of sFlt-1:PlGF complex on its own or in combination with free PlGF as a ratio, as compared with total sFlt-1 in predicting the onset of preeclampsia.

The results of ROC analysis provided in the lowermost data panel are based on only those patient samples collected within weeks 16-21 of gestation, the patients having been diagnosed as normal, with mild preeclampsia being categorized as normal in the analysis, or as having been diagnosed with severe preeclampsia. Areas under the ROC curves follow: free PlGF assay (0.7394), total sFlt-1 assay (0.5455), sFlt-1:PlGF complex assay (0.7636), total sFlt-1/free PlGF ratio (0.6848) and sFlt-1:PlGF complex/free PlGF ratio (0.8707). The results demonstrate the superior performance of sFlt-1:PlGF complex on its own or as a ratio, as compared to total sFlt-1 in predicting the onset of preeclampsia.

While particular embodiments of the invention have been shown, the invention is not limited thereto, since modifications may be made by those skilled in the art, particularly in light of the foregoing teachings. Reasonable variation and modification are possible within the scope of the foregoing disclosure of the invention without departing from the spirit of the invention.

The subject matter of all documents referenced in this disclosure including published patent applications, issued patents and non-patent publications and the subject matter of all references cited in these documents are incorporated herein by reference.

TABLE 1

Dose-Response Results

| sFlt-1:PlGF Complex Calibrator ID | sFlt-1:PlGF Complex Concentration (pg/mL) | Signal (ALU) |
|---|---|---|
| CR1 | 0 | 14.7 |
| CR2 | 75.0 | 20.8 |
| CR3 | 188 | 37.3 |
| CR4 | 375 | 76.3 |
| CR5 | 750 | 165 |
| CR6 | 1500 | 365 |
| CR7 | 3125 | 869 |
| CR8 | 6250 | 1723 |
| CR9 | 12500 | 3628 |
| CR10 | 25000 | 7292 |

TABLE 2

Cross reactivity of Free sFlt-1

| sFlt-1 Concentration (pg/mL) | Sample ID | Signal (ALU) | Predicted Concentration (pg/mL) | % Cross Reactivity |
|---|---|---|---|---|
| 0 | S R1B | 15.36 | 29.33 | N/A |
| 0 | S R1H | 11.02 | 6.181 | N/A |
| 100 | S R2 | 12.24 | 13.52 | 13.5 |
| 500 | S R3 | 6.96 | 0.00 | 0.0 |
| 1000 | S R4 | 11.57 | 9.614 | 1.0 |
| 2000 | S R5 | 16.30 | 33.56 | 1.7 |
| 10000 | S R6 | 22.29 | 57.23 | 0.6 |
| 20000 | S R7 | 13.19 | 18.68 | 0.1 |
| 40000 | S R8 | 17.78 | 39.84 | 0.1 |
| 80000 | S R9 | 33.82 | 95.54 | 0.1 |
| 160000 | S R10 | 60.84 | 174.5 | 0.1 |

TABLE 3

Cross Reactivity of Free PlGF

| PlGF Concentration (pg/mL) | Sample ID | Signal (ALU) | Predicted concentration (pg/mL) | % Cross Reactivity |
|---|---|---|---|---|
| 0 | P R1S | 14.97 | 27.5 | N/A |
| 0 | P R1B | 18.60 | 43.2 | N/A |
| 56 | P R2 | 11.56 | 9.57 | 17.1 |
| 112 | P R3 | 12.49 | 14.9 | 13.3 |
| 446 | P R4 | 10.24 | 1.04 | 0.2 |
| 1115 | P R5 | 10.57 | 3.28 | 0.3 |
| 2231 | P R6 | 10.45 | 2.48 | 0.1 |
| 11154 | P R7 | 11.46 | 8.91 | 0.1 |
| 22307 | P R8 | 21.67 | 54.9 | 0.2 |

TABLE 4

Patient results: sFlt-1:PlGF complex, free PlGF and sFlt-1:PlGF complex/free PlGF ratio

| Sample ID | Gestational Age at Collection (weeks) | Diagnosis | Classification (1 = preeclampsia, 0 = normal) | sFlt-1:PlGF Complex Concentration (pg/mL) | Free PlGF Concentration (pg/mL) | sFlt-1:PlGF Complex/Free PlGF Ratio |
|---|---|---|---|---|---|---|
| N47 | 23¾ | preeclampsia | 1 | 316 | 23.3 | 13.6 |
| N49 | 35 | preeclampsia | 1 | 3553 | 72.4 | 49.1 |
| N50 | 30⁶/₇ | preeclampsia | 1 | 1421 | 6.16 | 230.7 |
| N51 | 21½ | preeclampsia w/HELLP | 1 | 717 | 5 | 143.3 |
| N52 | 33⁴/₇ | preeclampsia | 1 | 79 | 4.02 | 19.6 |
| N53 | 25³/₇ | preeclampsia w/HELLP | 1 | 432 | 5 | 86.4 |
| N54 | 29 | preeclampsia w/HELLP | 1 | 1093 | 5 | 218.6 |
| N55 | 26⁵/₇ | preeclampsia | 1 | 2437 | 27.2 | 89.6 |

TABLE 4-continued

Patient results: sFlt-1:PlGF complex, free PlGF and sFlt-1:PlGF complex/free PlGF ratio

| Sample ID | Gestational Age at Collection (weeks) | Diagnosis | Classification (1 = preeclampsia, 0 = normal) | sFlt-1:PlGF Complex Concentration (pg/mL) | Free PlGF Concentration (pg/mL) | sFlt-1:PlGF Complex/Free PlGF Ratio |
|---|---|---|---|---|---|---|
| N56 | 33 5/7 | preeclampsia | 1 | 2031 | 158 | 12.9 |
| N58 | 38 4/7 | normal | 0 | 6 | 74.5 | 0.1 |
| N59 | 22 | normal | 0 | 170 | 129 | 1.3 |
| N60 | 38 6/7 | normal | 0 | 1122 | 508 | 2.2 |
| N61 | 36 2/7 | normal | 0 | 42 | 40.5 | 1.0 |
| N62 | 29 3/7 | gestational hypertension + preeclampsia | 1 | 5629 | 45.9 | 122.6 |
| N63 | 30 | IUGR + gestational hypertension | 0 | 1332 | 6.25 | 213.1 |
| N64 | 36 | normal | 0 | 629 | 32.1 | 19.6 |
| N65 | 32 5/7 | normal | 0 | 281 | 36.5 | 7.7 |
| N67 | 39 | normal | 0 | 5 | 5 | 1.0 |
| N68 | 37 5/7 | normal | 0 | 446 | 320 | 1.4 |

TABLE 5

ROC Analysis

| | SFlt-1:PlGF Complex Assay |
|---|---|
| W: | 0.8000 |
| SE: | 0.1017 |
| p: | 0.0016 |

W = Area Under Curve,
SE = Standard Error,
p = probability

TABLE 6

ROC Analysis

| | sFlt-1:PlGF/free PlGF ratio |
|---|---|
| W: | 0.889 |
| SE: | 0.0886 |
| p: | <0.0001 |

W = Area Under Curve,
SE = Standard Error,
p = probability

TABLE 7

| Analyte Measured | Total sFlt-1 | Free sFlt-1 | sFlt-1:PlGF complex | Total PlGF | Free PlGF | SFlt-1:PlGF complex |
|---|---|---|---|---|---|---|
| Coated on ELISA well | sFlt-1 specific monoclonal antibody (49560, R&D Systems) binds to Free sFlt-1 and sFlt-1:PlGF Complex | | | PlGF specific monoclonal antibody (358932, R&D Systems) binds to Free PlGF and sFlt-1:PlGF Complex | | |
| sample | Preincubated sample containing 2000 pg/mL sFlt-1 and 0-2000 pg/mL PlGF | | | Preincubated sample containing 2000 pg/mL PlGF and 0-2000 pg/mL sFlt-1 | | |
| HRP detection antibody (1 µg/mL) | M14 Ortho-clinical diagnostics | 49566 R&D Systems | 358905 R&D Systems | 358905 R&D Systems | 37203 R&D systems | M14 Ortho-clinical diagnostics |
| Detection antibody characteristic | Binds to free sFlt-1 and sFlt-1:PlGF complex | Binds free sFlt-1 but not to sFlt-1:PlGF complex | Binds to free PlGF and sFlt-1:PlGF complex | Binds to free PlGF and sFlt-1:PlGF complex | Binds to free PlGF but not to sFlt-1:PlGF complex | Binds to free sFlt-1 and sFlt-1:PlGF complex |

TABLE 8

| | | Absorbance 492 nm | | |
|---|---|---|---|---|
| sFlt (pg/mL) | PlGF (pg/mL) | Total sFlt-1 | Free sFlt-1 | sFlt-1:PlGF complex |
| 0 | 0 | 0.104 | 0.095 | 0.006 |
| 2000 | 2000 | 2.163 | 1.077 | 0.734 |
| 2000 | 200 | 2.144 | 1.215 | 0.176 |
| 2000 | 20 | 2.198 | 1.601 | 0.096 |
| 2000 | 2 | 2.246 | 1.895 | 0.070 |
| 2000 | 0 | 2.290 | 1.976 | 0.014 |

Plate coated with 1 µg/mL anti-sFlt-1 monoclonal antibody 49560, R&D Systems

TABLE 9

| | | Absorbance 492 nm | | |
|---|---|---|---|---|
| PlGF (pg/mL) | SFlt-1 (pg/mL) | Total PlGF | Free PlGF | sFlt:PlGF complex |
| 0 | 0 | 0.001 | 0.004 | 0.022 |
| 2000 | 2000 | 3.000 | 1.908 | 1.185 |
| 2000 | 200 | 3.000 | 2.087 | 0.164 |
| 2000 | 20 | 3.000 | 2.146 | 0.017 |
| 2000 | 2 | 3.000 | 2.289 | 0.008 |
| 2000 | 0 | 3.000 | 3.000 | 0.002 |

Plate Coated with 0.8 µg/mL anti-PlGF rat monoclonal 358932, R&D Systems

TABLE 10 sFlt-1:PlGF complex, sFlt-1, free PlGF and Ratios
Gestation Age: Weeks 27-37

| Subject ID | Gestational Age At Collection (Weeks) | Preeclampsia (1 = Yes, 0 = No) | RDS ELISA Free PlGF | RDS ELISA Total sFlt-1 | sFlt-1:PlGF Complex | RDS ELISA Total sFlt-1/RDS ELISA Free PlGF Ratio | sFlt-1:PlGF Complex/RDS ELISA Free PlGF Ratio |
|---|---|---|---|---|---|---|---|
| 1 | 34.3 | 1 | 247 | 3127 | 652 | 12.7 | 2.6 |
| 7 | 34.9 | 0 | 938 | 1854 | 189 | 2.0 | 0.2 |
| 2 | 29.7 | 1 | 41.3 | 68920 | 1430 | 1667.7 | 34.6 |
| 9 | 30.1 | 0 | 469 | 900 | 92.3 | 1.9 | 0.2 |
| 3 | 37.0 | 1 | 66.8 | 16079 | 1300 | 240.5 | 19.4 |
| 8 | 36.1 | 0 | 144 | 36830 | 5960 | 255.5 | 41.3 |
| 6 | 30.1 | 1 | 77.8 | 46935 | 2430 | 603.5 | 31.2 |
| 14 | 31.1 | 0 | 870 | 1714 | 193 | 2.0 | 0.2 |
| 11 | 27.0 | 1 | 39.3 | 6906 | 559 | 175.8 | 14.2 |
| 15 | 27.1 | 0 | 256 | 2602 | 195 | 10.2 | 0.8 |
| 10 | 34.6 | 1 | 351 | 1716 | 219 | 4.9 | 0.6 |
| 12 | 34.6 | 0 | 60.5 | 8462 | 855 | 139.9 | 14.1 |
| 13 | 37.0 | 1 | 212 | 9699 | 1870 | 45.7 | 8.8 |
| 38 | 37.4 | 0 | 311 | 4376 | 794 | 14.1 | 2.6 |
| 17 | 37.4 | 1 | 33.0 | 8303 | 357 | 251.9 | 10.8 |
| 19 | 37.4 | 0 | 184 | 4165 | 499 | 22.6 | 2.7 |
| 21 | 37.0 | 1 | 58.7 | 13435 | 1250 | 228.8 | 21.3 |
| 39 | 37.4 | 0 | 263 | 1487 | 380 | 5.7 | 1.4 |
| 22 | 29.0 | 1 | 85.3 | 15223 | 2000 | 178.4 | 23.4 |
| 34 | 28.6 | 0 | 1443 | 3290 | 478 | 2.3 | 0.3 |
| 23 | 36.4 | 1 | 131 | 6256 | 1270 | 47.7 | 9.7 |
| 24 | 36.6 | 0 | 1622 | 7180 | 826 | 4.4 | 0.5 |
| 27 | 29.7 | 1 | 37.2 | 14040 | 998 | 377.9 | 26.9 |
| 35 | 29.9 | 0 | 883 | 1790 | 332 | 2.0 | 0.4 |
| 28 | 30.3 | 1 | 100 | 13350 | 1880 | 133.2 | 18.8 |
| 5 | 30.0 | 0 | 627 | 5214 | 391 | 8.3 | 0.6 |
| 29 | 31.3 | 0 | 1789 | 2422 | 433 | 1.4 | 0.2 |
| 30 | 31.3 | 1 | 51.5 | 34730 | 1630 | 674.3 | 31.6 |
| 31 | 31.3 | 1 | 43.6 | 4745 | 259 | 108.9 | 5.9 |
| 33 | 31.4 | 0 | 1084 | 3080 | 602 | 2.8 | 0.6 |
| 16 | 33.4 | 1 | 1460 | 2106 | 492 | 1.4 | 0.3 |
| 18 | 32.6 | 0 | 1324 | 1687 | 260 | 1.3 | 0.2 |
| 26 | 31.1 | 1 | 379 | 1530 | 374 | 4.0 | 1.0 |
| 41 | 32.1 | 0 | 548 | 1454 | 229 | 2.7 | 0.4 |
| 36 | 30.6 | 1 | 29.9 | 27790 | 934 | 930.3 | 31.3 |
| 4 | 30.0 | 0 | 900 | 2016 | 506 | 2.2 | 0.6 |
| | | W: | 0.8796 | 0.7994 | 0.7654 | 0.8519 | 0.8642 |
| | | SE: | 0.0604 | 0.0769 | 0.0826 | 0.0669 | 0.0669 |
| | | p: | <0.0001 | <0.0001 | 0.0007 | <0.0001 | <0.0001 |
| | | n | 36 | 36 | 36 | 36 | 36 |

TABLE 11 sFlt-1:PlGF-1 complex, sFlt-1, Free PlGF and Ratios
Gestation Age: Weeks 13-21
(continues on next 3 pages)

| Specimen No. | Gestational Age at Collection (weeks) | Mild or Severe PE (ICD9 Codes 642.01, 642.41, 2652.43, 642.71, 642.91, 642.51) | Severe PE with delivery (ICD9 Code 642.51) | Conc (pg/mL) RDS ELISA Free PlGF | RDS ELISA Total sFlt-1 | sFlt-1:PlGF Compex | RDS ELISA Total sFlt-1/RDS ELISA Free PlGF Ratio | sFlt-1:PlGF Comploex/ RDS ELISA Free PlGF Ratio |
|---|---|---|---|---|---|---|---|---|
| URMC618 | 12.57 | 1 | 1 | 45.3 | 1742 | 3.4 | 38.5 | 0.1 |
| URMC619 | 12.86 | 0 | 0 | 210 | 2155 | 81.6 | 10.3 | 0.4 |
| URMC594 | 14.14 | 0 | 0 | 40.5 | 1421 | 59.2 | 35.1 | 1.5 |
| URMC592 | 14.29 | 1 | 1 | 44.9 | 2402 | 142 | 53.6 | 3.2 |
| URMC606 | 14.29 | 0 | 0 | 97.5 | 1910 | 72.2 | 19.6 | 0.7 |
| URMC624 | 14.29 | 1 | 1 | 42.2 | 3208 | 256 | 76.1 | 6.1 |
| URMC664 | 14.29 | 0 | 0 | 161 | 2066 | 51.5 | 12.8 | 0.3 |
| URMC625 | 14.43 | 0 | 0 | 56.2 | 3169 | 61.1 | 56.4 | 1.1 |
| URMC663 | 14.57 | 1 | 0 | 44.1 | 1712 | 53.4 | 38.8 | 1.2 |
| URMC604 | 14.86 | 1 | 0 | 127 | 1179 | 7.7 | 9.3 | 0.1 |
| URMC527 | 15.00 | 1 | 0 | 75.4 | 2234 | 68.3 | 29.6 | 0.9 |
| URMC529 | 15.00 | 0 | 0 | 35.9 | 1378 | 100 | 38.4 | 2.8 |
| URMC545 | 15.00 | 1 | 0 | 59.5 | 2053 | 46.1 | 34.5 | 0.8 |
| URMC621 | 15.00 | 1 | 0 | 145 | 4200 | 186 | 29.0 | 1.3 |
| URMC547 | 15.14 | 0 | 0 | 75.3 | 3440 | 123 | 45.7 | 1.6 |
| URMC587 | 15.14 | 0 | 0 | 53.1 | 1367 | 70.7 | 25.7 | 1.3 |
| URMC623 | 15.14 | 0 | 0 | 39.4 | 1768 | 31.5 | 44.9 | 0.8 |
| URMC645 | 15.29 | 1 | 0 | 38.4 | 1860 | 41.8 | 48.5 | 1.1 |
| URMC647 | 15.29 | 0 | 0 | 53.4 | 2805 | 109 | 52.5 | 2.0 |
| URMC651 | 15.29 | 1 | 0 | 112 | 2853 | 103 | 25.5 | 0.9 |
| URMC586 | 15.43 | 1 | 0 | 20.7 | 5201 | 119 | 251.6 | 5.8 |
| URMC653 | 15.43 | 0 | 0 | 92.2 | 1431 | 41.1 | 15.5 | 0.4 |
| URMC601 | 15.57 | 1 | 0 | 53.1 | 1192 | 43.2 | 22.5 | 0.8 |
| URMC613 | 15.57 | 1 | 1 | 101 | 1499 | 25.3 | 14.9 | 0.3 |
| URMC668 | 15.57 | 0 | 0 | 108 | 2091 | 188 | 19.4 | 1.7 |
| URMC570 | 15.71 | 0 | 0 | 39.9 | 939 | −1.23 | 23.5 | 0.0 |
| URMC603 | 15.71 | 0 | 0 | 59.1 | 2281 | 35.3 | 38.6 | 0.6 |
| URMC614 | 15.71 | 0 | 0 | 206 | 1302 | 59.3 | 6.3 | 0.3 |
| URMC568 | 15.86 | 1 | 0 | 160 | 1526 | 119 | 9.5 | 0.7 |
| URMC666 | 15.86 | 1 | 0 | 76.9 | 1915 | 92.4 | 24.9 | 1.2 |
| URMC638 | 16.00 | 0 | 0 | 96.0 | 5102 | 95.2 | 53.1 | 1.0 |
| URMC515 | 16.14 | 1 | 0 | 94.2 | 2754 | 166 | 29.2 | 1.8 |
| URMC517 | 16.14 | 0 | 0 | 99.8 | 2649 | 55.2 | 26.5 | 0.6 |
| URMC577 | 16.14 | 1 | 0 | 225 | 2297 | 173 | 10.2 | 0.8 |
| URMC579 | 16.14 | 0 | 0 | 101 | 3007 | 67.9 | 29.8 | 0.7 |
| URMC633 | 16.14 | 1 | 0 | 92.2 | 2860 | 104 | 31.0 | 1.1 |
| URMC692 | 16.14 | 1 | 0 | 26.8 | 1303 | 44.3 | 48.5 | 1.7 |
| URMC533 | 16.29 | 1 | 0 | 143 | 1458 | 110 | 10.2 | 0.8 |
| URMC534 | 16.29 | 0 | 0 | 105 | 3248 | 95.8 | 30.9 | 0.9 |
| URMC574 | 16.29 | 1 | 0 | 157 | 4192 | 78.7 | 26.7 | 0.5 |
| URMC590 | 16.29 | 0 | 0 | 120 | 1381 | 106 | 11.5 | 0.9 |
| URMC634 | 16.29 | 0 | 0 | 266 | 1941 | 91.9 | 7.3 | 0.3 |
| URMC684 | 16.29 | 1 | 0 | 118 | 1475 | 63.1 | 12.5 | 0.5 |
| URMC685 | 16.29 | 0 | 0 | 89.0 | 931 | 16.2 | 10.5 | 0.2 |
| URMC636 | 16.43 | 1 | 0 | 184 | 1961 | 73.8 | 10.7 | 0.4 |
| URMC648 | 16.43 | 1 | 0 | 121 | 1786 | 76.3 | 14.7 | 0.6 |
| URMC650 | 16.43 | 0 | 0 | 69.7 | 1749 | 35.6 | 25.1 | 0.5 |
| URMC536 | 16.57 | 1 | 0 | 129 | 2358 | 130 | 18.3 | 1.0 |
| URMC571 | 16.57 | 1 | 0 | 58.9 | 2575 | 643 | 43.7 | 10.9 |
| URMC573 | 16.57 | 0 | 0 | 68.3 | 3304 | 68.3 | 48.4 | 1.0 |
| URMC589 | 16.57 | 1 | 1 | 15.1 | 2293 | 322 | 151.9 | 21.3 |
| URMC669 | 16.57 | 1 | 1 | 47.8 | 2373 | 105 | 49.6 | 2.2 |
| URMC676 | 16.57 | 0 | 0 | 63.7 | 2353 | 88.1 | 36.9 | 1.4 |
| URMC509 | 16.71 | 1 | 0 | 93.8 | 429 | 24.3 | 4.6 | 0.3 |
| URMC538 | 16.71 | 0 | 0 | 113 | 2999 | 118 | 26.6 | 1.0 |
| URMC671 | 16.71 | 0 | 0 | 77.9 | 754 | −0.422 | 9.7 | 0.0 |
| URMC511 | 16.86 | 0 | 0 | 192 | 3341 | 136 | 17.4 | 0.7 |
| URMC512 | 16.86 | 1 | 0 | 53.5 | 754 | −1.44 | 14.1 | 0.0 |
| URMC513 | 16.86 | 0 | 0 | 170 | 1152 | 68.9 | 6.8 | 0.4 |
| URMC542 | 16.86 | 1 | 0 | 155 | 13220 | 258 | 85.1 | 1.7 |
| URMC543 | 16.86 | 0 | 0 | 86.5 | 2299 | 84.1 | 26.6 | 1.0 |
| URMC576 | 16.86 | 0 | 0 | 169 | 4417 | 140 | 26.2 | 0.8 |
| URMC597 | 17.00 | 0 | 0 | 138 | 1960 | 99.9 | 14.2 | 0.7 |
| URMC610 | 17.00 | 1 | 1 | 121 | 2389 | 339 | 19.8 | 2.8 |
| URMC612 | 17.00 | 0 | 0 | 70.9 | 1920 | 52.8 | 27.1 | 0.7 |
| URMC595 | 17.29 | 1 | 0 | 62.9 | 2355 | 100 | 37.4 | 1.6 |
| URMC657 | 17.29 | 1 | 0 | 114 | 1212 | 92.1 | 10.7 | 0.8 |
| URMC691 | 17.29 | 0 | 0 | 113 | 2191 | 104 | 19.4 | 0.9 |
| URMC643 | 17.43 | 0 | 0 | 222 | 5476 | 86 | 24.7 | 0.4 |

TABLE 11-continued sFlt-1:PlGF-1 complex, sFlt-1, Free PlGF and Ratios
Gestation Age: Weeks 13-21
(continues on next 3 pages)

| Specimen No. | Gestational Age at Collection (weeks) | Mild or Severe PE (ICD9 Codes 642.01, 642.41, 2652.43, 642.71, 642.91, 642.51) | Severe PE with delivery (ICD9 Code 642.51) | Conc (pg/mL) RDS ELISA Free PlGF | RDS ELISA Total sFlt-1 | sFlt-1:PlGF Compex | RDS ELISA Total sFlt-1/RDS ELISA Free PlGF Ratio | sFlt-1:PlGF Comploex/ RDS ELISA Free PlGF Ratio |
|---|---|---|---|---|---|---|---|---|
| URMC672 | 17.43 | 1 | 0 | 247 | 3125 | 123 | 12.7 | 0.5 |
| URMC521 | 17.57 | 1 | 1 | 46.4 | 346 | 12.7 | 7.4 | 0.3 |
| URMC560 | 17.57 | 0 | 0 | 211 | 1754 | 70.9 | 8.3 | 0.3 |
| URMC642 | 17.57 | 1 | 1 | 153 | 2390 | 183 | 15.6 | 1.2 |
| URMC522 | 17.71 | 0 | 0 | 247 | 3507 | 116 | 14.2 | 0.5 |
| URMC551 | 17.71 | 1 | 1 | 251 | 4549 | 448 | 18.2 | 1.8 |
| URMC659 | 17.86 | 0 | 0 | 97.4 | 1457 | 74.3 | 15.0 | 0.8 |
| URMC539 | 18.00 | 1 | 0 | 129 | 697 | 33.9 | 5.4 | 0.3 |
| URMC541 | 18.00 | 0 | 0 | 115 | 1317 | 127 | 11.5 | 1.1 |
| URMC530 | 18.29 | 1 | 1 | 89.2 | 1222 | 142 | 13.7 | 1.6 |
| URMC678 | 18.29 | 1 | 0 | 254 | 1893 | 224 | 7.4 | 0.9 |
| URMC630 | 18.43 | 1 | 0 | 204 | 2461 | 116 | 12.0 | 0.6 |
| URMC679 | 18.43 | 0 | 0 | 445 | 2478 | 206 | 5.6 | 0.5 |
| URMC531 | 18.57 | 0 | 0 | 148 | 3006 | 19.1 | 20.3 | 0.1 |
| URMC564 | 18.71 | 1 | 1 | 64.9 | 1969 | 80.3 | 30.4 | 1.2 |
| URMC565 | 18.71 | 0 | 0 | 71.6 | 2653 | 23.4 | 37.0 | 0.3 |
| URMC640 | 18.71 | 0 | 0 | 161 | 1411 | 42.8 | 8.8 | 0.3 |
| URMC632 | 18.86 | 0 | 0 | 166 | 2573 | 79.2 | 15.5 | 0.5 |
| URMC639 | 18.86 | 1 | 0 | 67.8 | 435 | −4.36 | 6.4 | −0.1 |
| URMC616 | 19.00 | 0 | 0 | 329 | 1538 | 51.2 | 4.7 | 0.2 |
| URMC518 | 19.29 | 1 | 0 | 280 | 4100 | 212 | 14.6 | 0.8 |
| URMC615 | 19.57 | 1 | 1 | 33.8 | 11565 | 391 | 342.6 | 11.6 |
| URMC519 | 19.71 | 0 | 0 | 217 | 878 | 102 | 4.1 | 0.5 |
| URMC505 | 20.43 | 0 | 0 | 279 | 856 | 71.9 | 3.1 | 0.3 |
| URMC503 | 21.14 | 1 | 0 | 483 | 1762 | 156 | 3.6 | 0.3 |

TABLE 12

ROC Analysis

| | RDS ELISA Free PlGF | RDS ELISA Total sFlt-1 | sFlt-1:PlGF Complex | RDS ELISA Total sFlt-1/ RDS ELISA Free PlGF Ratio | sFlt-1:PlGF Complex/ RDS ELISA Free PlGF Ratio |
|---|---|---|---|---|---|
| Mild or Severe PE vs. No PE (Gestation Age at Collection 13-21) | | | | | |
| W: | 0.5745 | 0.5029 | 0.6331 | 0.5396 | 0.6392 |
| SE: | 0.0594 | 0.0602 | 0.0591 | 0.0599 | 0.0578 |
| p: | 0.1050 | 0.4805 | 0.0122 | 0.2543 | 0.0080 |
| n: | 94 | 94 | 94 | 94 | 94 |
| Severe PE (Mild PE = Normal, Gestation Age at Collection 13-21)) | | | | | |
| W: | 0.7142 | 0.5622 | 0.6942 | 0.6771 | 0.7445 |
| SE: | 0.0819 | 0.0854 | 0.1029 | 0.0838 | 0.1004 |
| p: | 0.0045 | 0.2333 | 0.0296 | 0.0173 | 0.0075 |
| n: | 94 | 94 | 94 | 94 | 94 |
| Severe PE (Mild PE = Normal, Gestation Age at Collection 16-21)) | | | | | |
| W: | 0.7394 | 0.5455 | 0.7636 | 0.6848 | 0.8707 |
| SE: | 0.1041 | 0.1073 | 0.1044 | 0.0963 | 0.0847 |
| p: | 0.0108 | 0.3360 | 0.0058 | 0.0274 | <0.0001 |
| n: | 64 | 64 | 64 | 64 | 64 |

We claim:

1. A composition for determining the presence or amount of sFlt-1:PlGF complex, the composition consisting of a single capture agent and a single detector agent, wherein the single capture agent and the single detector agent consist of:

a) a single capture agent that binds to PlGF and a single detector agent that binds to one or both of sFlt-1 and sFlt-1:PlGF complex; or b) a single capture agent that binds to sFlt-1 and a single detector agent that binds to one or both of PlGF and sFlt-1:PlGF complex; or c) a single capture agent that binds to sFlt-1:PlGF complex and a single detector agent that binds to sFlt-1:PlGF complex, wherein the single capture agent and the single detector agent are capable of being bound simultaneously to the complex; or d) a single capture agent that binds to sFlt-1:PlGF complex and a single detector agent that binds to one or both of PlGF and sFlt-1.

2. The composition of claim 1 wherein PlGF is PlGF-1, PlGF-2, or PlGF-3.

3. The composition of claim 1 wherein one or both of capture agent and detector agent are polyclonal antibodies.

4. The composition of claim 1 wherein one or both of capture agent and detector agent are monoclonal antibodies.

5. The composition of claim 1 wherein one of the capture agent and detector agent is a monoclonal antibody and the other of the capture agent and detector agent is a polyclonal antibody.

\* \* \* \* \*